United States Patent [19]

Hauptmann et al.

[11] Patent Number: 4,917,887
[45] Date of Patent: Apr. 17, 1990

[54] HYBRID INTERFERONS, THEIR USE AS PHARMACEUTICAL COMPOSITIONS AND AS INTERMEDIATE PRODUCTS FOR THE PREPARATION OF ANTIBODIES AND THE USE THEREOF AND PROCESSES FOR PREPARING THEM

[75] Inventors: Rudolf Hauptmann, Ebreichsdorf; Peter Swetly, Vienna; Peter Meindl, Vienna; Gunther Adolf, Vienna; Edgar Falkner, Vienna; Gerhard Bodo, Vienna; Ingrid Maurer-Fogy, Vienna, all of Austria

[73] Assignee: Boehringer Ingelheim International GmbH, Fed. Rep. of Germany

[21] Appl. No.: 23,634

[22] Filed: Mar. 9, 1987

[30] Foreign Application Priority Data

Mar. 10, 1986 [DE] Fed. Rep. of Germany ....... 3607835

[51] Int. Cl.$^4$ ...................... A61K 45/02; C07K 13/00; C07K 15/26; C12P 21/00
[52] U.S. Cl. ..................................... 424/85.7; 530/351
[58] Field of Search .......................... 530/351; 435/68; 424/85.4, 85.5, 85.6, 85.7

[56] References Cited

U.S. PATENT DOCUMENTS 4,414,150 11/1983 Goeddel ............................ 424/85.7
4,456,748 6/1984 Goeddel ............................ 424/85.7

FOREIGN PATENT DOCUMENTS 0051873 5/1982 European Pat. Off. .
0174143 3/1986 European Pat. Off. .
WO80/02229 10/1980 PCT Int'l Appl. .
WO83/02461 7/1983 PCT Int'l Appl. .
85/05759 2/1986 South Africa .

OTHER PUBLICATIONS

Fish, E. N. et al., *J. Interferon Res.*, 9:97–114, (1989).
Rehberg, E. et al., *J. Biol. Chem.*, 257:11497–11502, (1982).
Shepard, H., et al., Nature, vol. 294, pp. 563–565, 1981.
Hauptmann, R. et al., *Nucl. Acids. Res.*, 13:4739–4749, (1985).
Shepard, H. M. et al., *Antiviral Res.*, 4:4, (1984).
Capon, D. J. et al., *Chemical Abstracts*, 102:216181g, (1985).

Primary Examiner—Blondel Hazel
Attorney, Agent, or Firm—Saidman, Sterne, Kessler & Goldstein

[57] ABSTRACT

This invention relates to new hybrid interferons consisting of part of an α-interferon and part of an omega interferon, the N-terminal Met or N-formyl-Met derivatives thereof and, if the peptide sequence of the hybrid interferon contains a glycosylation site, the N-glycosylated derivatives thereof, their use as pharmaceutical compositions and as intermediate products for immunizing experimental animals and processes for producing them, new monoclonal antibodies and their use in purifying α and omega-interferons, the hybrid cell lines which secrete them and processes for preparing them, a new process for purifying α and omega-interferons by means of a new antibody affinity column containing the above-mentioned new monoclonal antibodies, and processes for the preparation thereof, new hybrid plasmids for improving the expression of omega-interferons and new intermediate plasmids for preparing the new plasmids and processes for the preparation thereof.

8 Claims, 9 Drawing Sheets

HYBRID INTERFERONS, THEIR USE AS PHARMACEUTICAL COMPOSITIONS AND AS INTERMEDIATE PRODUCTS FOR THE PREPARATION OF ANTIBODIES AND THE USE THEREOF AND PROCESSES FOR PREPARING THEM

FIELD OF THE INVENTION

The present invention relates to novel hybrid interferons of the formula

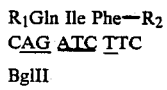
(I)

wherein BglII indicates the common BglII restriction site of the alpha 1-, alpha 2- and omega-interferons, $R_1$ and $R_2$ are a peptide sequence of an alpha 1- or alpha 2-interferon, or an omega-interferon. The invention also relates to use of these hybrid interferons in pharmaceutical compositions and as intermediate products for immunizing experimental animals, the DNA sequences coding for these hybrid interferons and processes for preparing them. The invention also relates to new monoclonal antibodies and the use thereof for purifying alpha- and omega-interferons, the hybrid cell lines which secrete them and processes for preparing them. The invention also relates to new plasmids for improving the expression of the omega-interferons, and new intermediate plasmids for preparing the new plasmids and processes for the preparation thereof.

Nucleic Acids Res. 13, 4739–4749 (1985) (see also EP-A-No. 0.170.204) describes a new class of type I interferons which are referred to as omega-interferons, the DNA sequences coding for them, plasmids which contain these DNA sequences, and organisms which produce the new interferons.

When producing fairly large test quantities of the new omega-interferons by means of the expression plasmids described in the above-mentioned publications, e.g. with pRHW11 or pRHW12 transformed in *E. coli* HB101, it was found, however, that it would be desirable to increase the expression of the new omega-interferons and at the same time improve the subsequent purification of the new expressed interferons required.

Surprisingly, it has now been found that these deficiencies can be remedied with new hybrid interferons consisting of part of an α-interferon and part of an omega-interferon, and by constructing a new plasmid with which the expression of the omega-interferons can be improved.

The new hybrid interferons, their N-terminal Met or N-formyl-Met derivatives and, if the peptide sequence of the hybrid interferon contains a glycosylation site, the N-glycosylated derivatives thereof have some superior pharmacological properties, but may be used particularly to prepare new monoclonal antibodies which are suitable for purifying α-and omega-interferons.

SUMMARY OF THE INVENTION

The present invention thus relates to new BglII-hybrid interferons of formula

(I)

wherein BglII indicates the common BglII restriction site of the α1, α2 and omega interferons, $R_1$ is the peptide sequence of an α1- or α2-interferon which is coded by the DNA sequence of these interferons in front of the BglII cutting site, and $R_2$ is the peptide sequence of an omega interferon which is coded by the DNA sequence of this interferon after the BglII cutting site, or $R_1$ is the peptide sequence of an omega-interferon which is coded by the DNA sequence of this interferon before the BglII cutting site, and $R_2$ is the peptide sequence of an α1- or α2-interferon which is coded by the DNA sequence of these interferons after the BglII cutting site, the N-terminal Met or N-formyl-Met derivatives thereof and, if the peptide sequence of the hybrid interferon contains a glycosylation site, the N-glycosylated derivatives thereof, their use as pharmaceutical compositions and as intermediate products for immunising experimental animals, the DNA sequences coding for these hybrid interferons and processes for preparing them, new monoclonal antibodies and the use thereof for purifying α- and omega-interferons, the hybrid cell lines which secrete them and processes for preparing them, a new method of purification for α and omega-interferons using a new antibody affinity column, containing the above-mentioned new monoclonal antibodies, and processes for the preparation thereof, new plasmids for improving the expression of the omega-interferons and new intermediate plasmids for preparing the new plasmids and processes for the preparation thereof.

According to the invention the following procedure is used to produce the objects specified above:

The first objective of this invention is to improve the purification of omega-interferons, particularly as nobody has yet succeeded in preparing a corresponding anti-omega-interferon-antibody-affinity column by known methods.

One way out of this situation is provided by the new hybrid interferons according to the invention, which are made up of one part of an α-interferon, preferably part of an α1 or α2-interferon, e.g. IFN-α2(Arg) (see EP-A-No. 0.095.702), and part of an omega interferon, preferably part of the omega1(Glu) or omega1(Gly) interferon (see EP-A-No. 0.170.204). In the case of IFN-α2(Arg) and IFN-omega1, the DNA sequences coding for the corresponding parts may be linked, for example, via the BglII cutting site which is in positions 191–196 in both genes. Any gap present must be included in the peptide of amino acids 1 to 66 of an α-interferon, e.g. the gap for the amino acid no. 45 in IFN-α2(Arg), so that the sequences of both genes may be compared with one another, as will be clear from the diagram which follows (including the N-terminal Met group which is usually split off again after the bacterial protein synthesis):

```
                 5                      10                      15
Met Cys Asp Leu Pro Gln Thr His Ser Leu Gly Ser Arg Arg Thr
ATG TGT GAT CTG CCT CAA ACC CAC AGC CTG GGT AGC AGG AGG ACC 45

Met Cys Asp Leu Pro Gln Asn His Gly Leu Leu Ser Arg Asn Thr
ATG TGT GAT CTG CCT CAG AAC CAT GGC CTA CTT AGC AGG AAC ACC 45

20                      15                      30
Leu Met Leu Leu Ala Gln Met Arg Arg Ile Ser Leu Phe Ser Cys
TTG ATG CTC CTG GCA CAG ATG AGG AGA ATC TCT CTT TTC TCC TGC 90

Leu Val Leu Leu His Gln Met Arg Arg Ile Ser Pro Phe Leu Cys
TTG GTG CTT CTG CAC CAA ATG AGG AGA ATC TCC CCT TTC TTG TGT 90

35                      40                      45
Leu Lys Asp Arg Arg Asp Phe Gly Phe Pro Gln Glu Glu Phe ...
TTG AAG GAC AGA CGT GAC TTT GGA TTT CCC CAG GAG GAG TTT ... 135

Leu Lys Asp Arg Arg Asp Phe Arg Phe Pro Gln Glu Met Val Lys
CTC AAG GAC AGA AGA GAC TTC AGG TTC CCC CAG GAG ATG GTA AAA 135

50                      55                      60
Gly Asn Gln Phe Gln Lys Ala Glu Thr Ile Pro Val Leu His Glu
GGC AAC CAG TTC CAA AAG GCT GAA ACC ATC CCT GTC CTC CAT GAG 180

Gly Ser Gln Leu Gln Lys Ala His Val Met Ser Val Leu His Glu
GGG AGC CAG TTG CAG AAG GCC CAT GTC ATG TCT GTC CTC CAT GAG 180

65                      70                      75
Met Ile Gln Gln Ile Phe Asn Leu Phe Ser Thr Lys Asp Ser Ser
ATG ATC CAG CAG ATC TTC AAT CTC TTC AGC ACA AAG GAC TCA TCT 225

Met Leu Gln Gln Ile Phe Ser Leu Phe His Thr Glu Arg Ser Ser
ATG CTG CAG CAG ATC TTC AGC CTC TTC CAC ACA GAG CGC TCC TCT 225

80                      85                      90
Ala Ala Trp Asp Glu Thr Leu Leu Asp Lys Phe Tyr Thr Glu Leu
GCT GCT TGG GAT GAG ACC CTC CTA GAC AAA TTC TAC ACT GAA CTC 270

Ala Ala Trp Asn Met Thr Leu Leu Asp Gln Leu His Thr Gly Leu
GCT GCC TGG AAC ATG ACC CTC CTA GAC CAA CTC CAC ACT GGA CTT 270

95                      100                     105
Tyr Gln Gln Leu Asn Asp Leu Glu Ala Cys Val Ile Gln Gly Val
TAC CAG CAG CTG AAT GAC CTG GAA GCC TGT GTG ATA CAG GGG GTG 315

His Gln Gln Leu Gln His Leu Glu Thr Cys Leu Leu Gln Val Val
CAT CAG CAA CTG CAA CAC CTG GAG ACC TGC TTG CTG CAG GTA GTG 315

110                     115                     120
Gly Val Thr Glu Thr Pro Leu Met Lys Glu Asp Ser Ile Leu Ala
GGG GTG ACA GAG ACT CCC CTG ATG AAG GAG GAC TCC ATT CTG GCT 360

Gly Glu Gly Glu Ser Ala Gly Ala Ile Ser Ser Pro Ala Leu Thr
GGA GAA GGA GAA TCT GCT GGG GCA ATT AGC AGC CCT GCA CTG ACC 360

125                     130                     135
Val Arg Lys Tyr Phe Gln Arg Ile Thr Leu Tyr Leu Lys Glu Lys
GTG AGG AAA TAC TTC CAA AGA ATC ACT CTC TAT CTG AAA GAG AAG 405

Leu Arg Arg Tyr Phe Gln Gly Ile Arg Val Tyr Leu Lys Glu Lys
TTG AGG AGG TAC TTC CAG GGA ATC CGT GTC TAC CTG AAA GAG AAG 405

140                     145                     150
Lys Tyr Ser Pro Cys Ala Trp Glu Val Val Arg Ala Glu Ile Met
AAA TAC AGC CCT TGT GCC TGG GAG GTT GTC AGA GCA GAA ATC ATG 450

Lys Tyr Ser Asp Cys Ala Trp Glu Val Val Arg Met Glu Ile Met
AAA TAC AGC GAC TGT GCC TGG GAA GTT GTC AGA ATG GAA ATC ATG 450

155                     160                     165
Arg Ser Phe Ser Leu Ser Thr Asn Leu Gln Glu Ser Leu Arg Ser
AGA TCT TTT TCT TTG TCA ACA AAC TTG CAA GAA AGT TTA AGA AGT 495

Lys Ser Leu Phe Leu Ser Thr Asn Met Gln Glu Arg Leu Arg Ser
AAA TCC TTG TTC TTA TCA ACA AAC ATG CAA GAA AGA CTG AGA AGT 495
```

```
                                                170
        Lys Glu
        AAG GAA TGA                                                           504
        Lys Asp Arg Asp Leu Gly Ser Ser
        AAA GAT AGA GAC CTG GGC TCA TCT TGA                                   522
```

In the above diagram, in each double row the first row represents the corresponding sequences of IFN-α2(Arg) and the second row represents those of omegal-interferon; the common BglII cutting site for both genes is located in nucleotide positions 191–196 - the IFN-α2(Arg) gene has a second BglII cutting site at nucleotide positions 451–456.

Moreover, the following representations of the individual plasmids, which are not to scale, contain only the essential sequences and restriction enzyme recognition sites. The following abbreviations have been used:

Restriction enzyme recognition sequences:
B: BamHI, Bg: BglII, Bg1: 1st BglII site in the IFN-α2(Arg) gene, Bg2: 2nd BglII site in the IFN-α2(Arg) gene, E: EcoRI, H: HindIII, N: NcoI, P: PstI, S: SphI
p/o: tryptophan promoter/operator (*Serratia marcescens*) with subsequent Shine-Dalgarno sequence (ribosomal binding site)
par: partition locus from the plasmid pPM31
ori: replication origin
Ap$^r$: Ampicillin resistance gene
Tc$^r$: Tetracycline resistance gene
Tc$^s$: Tetracycline sensitive
kb: 1000 base pairs

BRIEF DESCRIPTION OF THE DRAWINGS

The present application also contains the following figures.

DESCRIPTION OF THE PREFERRED EMBODIMENTS

Figure 1:
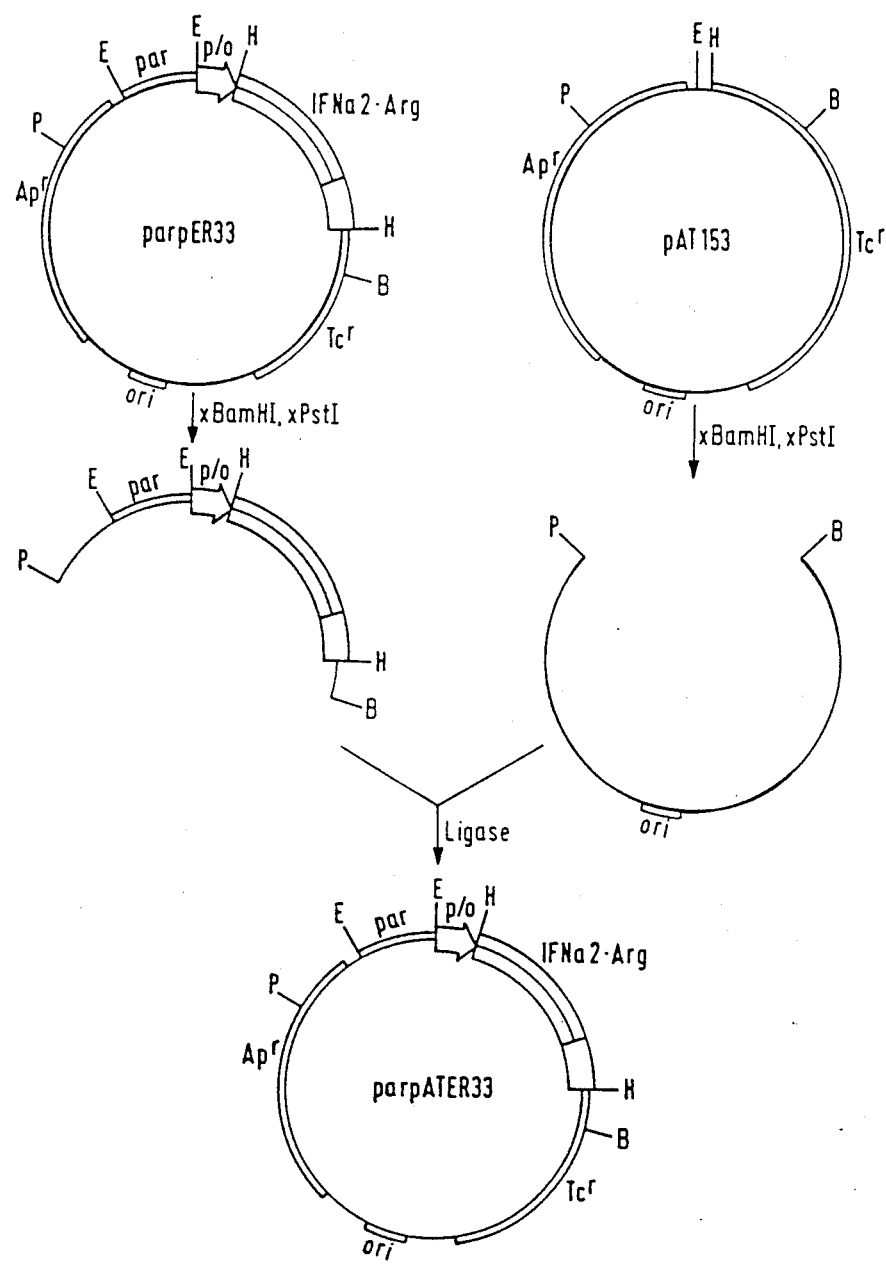
FIG. 1: construction scheme for parpATER33

Surprisingly, the new hybrid interferons are recognised by anti-IFN-α-antibodies. Consequently it is possible to purify the new hybrid interferons using anti-IFN-α-antibodies known from the literature (see for example EP-A-No. 0.119.476). With a pure new hybrid interferon thus obtained, it is possible to induce the formation of the corresponding antibody by immunising a test animal such as a BALB/c mouse. These new antibodies recognise not only the new hybrid interferons, but surprisingly also recognise the individual components of the hybrid interferons, e.g. an omega-interferon.

Thus, the starting basis for constructing the corresponding hybrid interferon plasmids is the common BglII restriction site in positions 191–196 of an α1-, α2- and omegal-interferon gene, as mentioned hereinbefore, the gap for codon no. 45 being counted in the IFN-α2(Arg) gene, and the basis for isolation of the corresponding gene required consists of the plasmids coding for an α1 or α2-interferon or for an omegal interferon.

For this purpose, according to the invention, first a new plasmid is produced which improves the expression of omegal interferon. The starting plasmids used may be the commercially available plasmid pAT153 known from the literature (made by Amersham, see also A. J. Twigg et al. in Nature 283, 216–218 (1980)), for example the plasmid parpER33 coding for IFN-α2(Arg) (see EP-A-No. 0.115.613) and a plasmid such as the plasmid pRHW11 or 12 (see EP-A-No. 0.170.204), coding for an omegal-interferon of formula

```
                  5                    10
Cys Asp Leu Pro Gln Asn His Gly Leu Leu Ser Arg Asn Thr 15              20              25
Leu Val Leu Leu His Gln Met Arg Arg Ile Ser Pro Phe Leu Cys 30              35              40
Leu Lys Asp Arg Arg Asp Phe Arg Phe Pro Gln Glu Met Val 45              50              55
Lys Gly Ser Gln Leu Gln Lys Ala His Val Met Ser Val Leu His 60              65              70
Glu Met Leu Gln Gln Ile Phe Ser Leu Phe His Thr Glu Arg Ser 75              80              85
Ser Ala Ala Trp Asn Met Thr Leu Leu Asp Gln Leu His Thr 90              95              100
Gly Leu His Gln Gln Leu Gln His Leu Glu Thr Cys Leu Leu 105             110             115
Gln Val Val Gly Glu Gly Glu Ser Ala —X— Ala Ile Ser Ser 120             125
Pro Ala Leu Thr Leu Arg Arg Tyr Phe Gln Gly Ile Arg Val 130             135             140
Tyr Leu Lys Glu Lys Lys Tyr Ser Asp Cys Ala Trp Glu Val Val 145             150             155
Arg Met Glu Ile Met Lys Ser Leu Phe Leu Ser Thr Asn Met Gln 160             165             170
          Glu Arg Leu Arg Ser Lys Asp Arg Asp Leu Gly Ser Ser
``` wherein X in position 111 represents Glu or Gly:

The plasmid parpER33 which contains the par-locus with the sequence of formula

```
    GAATTCCGAC AGTAAGACGG
      GTAAGCCTGT TGATGATACC
        GCTGCCTTAC                                                    50
```

```
TGGGTGCATT AGCCAGTCTG
     AATGACCTGT CACGGGATAA
           TCCGAAGTGG                    100

TCAGACTGGA AAATCAGAGG
     GCAGGAACTG CTGAACAGCA
           AAAAGTCAGA                    150

TAGCACCACA TAGCAGACCC
     GCCATAAAAC GCCCTGAGAA
           ZCCGTGACGG                    200

GCTTTTCTTG TATTATGGGT
     AGTTTCCTTG CATGAATCCA
           TAAAAGGCGC                    250

CTGTAGTGCC ATTTACCCCC
     ATTCACTGCC AGAGCCGTGA
           GCGCAGCGAA                    300

CTGAATGTCA CGAAAAAGAC
     AWCGACTCAG GTGCCTGATG
           GTCGGAGACA                    350

AAAGGAATAT TCAGCGATTT
     GCCCGAGGAA TTC                      383
``` wherein Z represents the nucleotide G or C and W represents the nucleotide G or no nucleotide, and the replicon and control sequences required for expression as characterised in claim 17, is cut with BamHI and PstI. The two fragments formed are separated by gel electrophoresis, e.g. with 1% agarose gel, and the smaller fragment which contains the IFN-α2(Arg) gene is isolated by electroelution. The resulting DNA is subsequently precipitated by the addition of ethanol, removed by centrifuging and taken up in a suitable buffer such as TE buffer, e.g. in 10 mMol of tri(hydroxymethyl)aminomethane (Tris), pH=8.0, and 1 mMol of ethylenediaminetetracetic acid disodium salt (EDTA).

The plasmid pAT153 is also cut with BamHI and PstI. The two fragments produced are separated by gel electrophoresis, e.g. with 1% agarose gel, and the larger fragment which contains the replication origin is isolated. The larger fragment thus obtained is then ligated with the smaller fragment obtained from the plasmid parpER33 in the presence of a ligase, e.g. T4 DNA ligase. In order to replicate the plasmids produced, bacteria, preferably E. coli of the HB101 strain (genotype F−, hsdS20(r−, m−), recA13, ara-14, proA2, lacY1, galK2, rpsL20 (Sm$^r$), xyl-5, mtl-1, supE44, lamba−), are washed with a CaCl$_2$ solution and the resulting competent E. coli HB101 are mixed with the ligase reaction mixture and after incubation at 0° C. the plasmid DNA is taken up by the bacteria by heat shock at 42° C. for 2 minutes. Subsequently, the transformed bacteria are plated on LB agar containing ampicillin (LB medium+15 g/l of agar). Only E. coli HB101 bacteria which have taken up a recombinant vector molecule are capable of growing on this agar. Using the above procedure, after incubation at 37° C., 12 resulting colonies were selected and the plasmids were isolated from them using the method of Birnboim et al. (see Nucl. Acids Res. 7, 1513 (1979)). By restriction enzyme double digestion of the selected plasmids with PstI-BamHI, PstI-PvuII or EcoRI-BamHI and subsequent gel electrophoresis of the resulting fragments, the correct construction of these plasmids was confirmed. A plasmid thus obtained was selected and designated parpATER33 (for the construction scheme see FIG. 1). This plasmid shows, transformed in E. coli HB101, the phenotype Ap$^r$ (ampicillin resistance), Tc$^r$ (tetracycline resistance).

The plasmid parpATER33 thus obtained having the following restriction map

Figure 2:
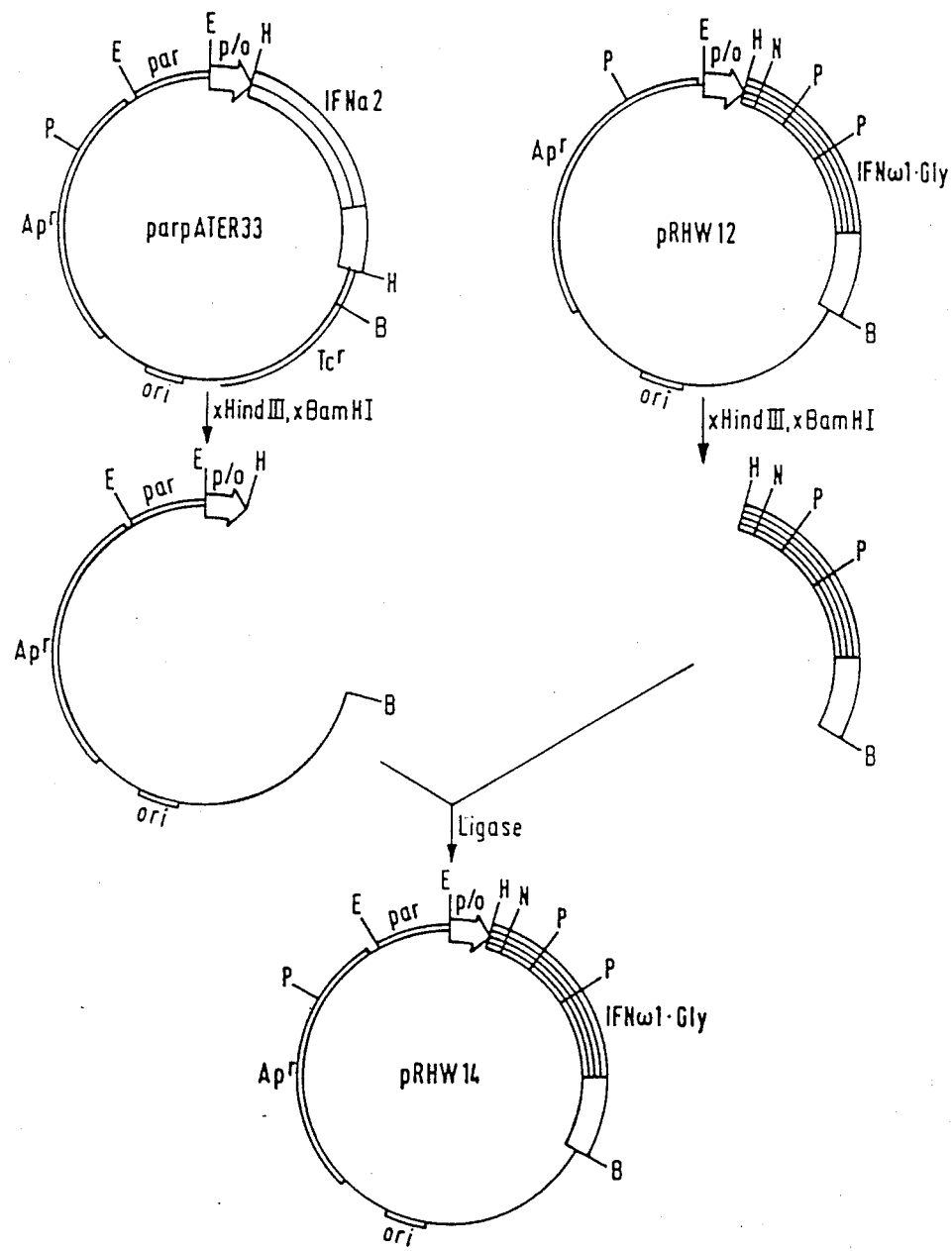
FIG. 2: construction scheme for pRHW14

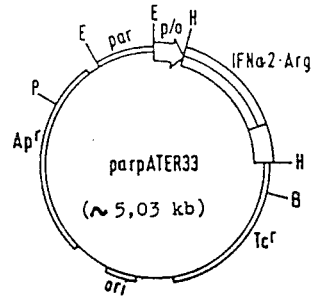

is cut with HindIII and BamHI in order to produce a plasmid which improves the expression of omegal-interferon (for the construction plan see FIG. 2). The three fragments thus produced are separated by gel electrophoresis, e.g. with 1% agarose gel and the largest fragment (fragment a) which is about 3750 base pairs (bp) long and which carries the tryptophan promoter/operator (Serratia marcescens), the replication origin and the Ap$^r$ gene is isolated and ligated with the DNA coding for an omegal-interferon. This DNA is obtained by cutting a plasmid which codes for omegal-interferon, preferably by cutting the plasmid pRHW11 or pRHW12 with BamHI and HindIII and subsequently separating the two fragments thus obtained by gel electrophoresis, the desired gene being contained in the smaller fragment which is about 800 bp long. In order to replicate the plasmids produced, bacteria, preferably E. coli HB101, are washed with a CaCl$_2$ solution and the competent E. coli HB101 thus obtained is mixed with the ligase reaction mixture and after incubation at 0° C. the plasmid DNA is taken up by the bacteria by heat shock at 42° C. for 2 minutes. Then the transformed bacteria are plated onto LB agar which contains ampicillin. Only E. coli HB101 bacteria which have absorbed a recombinant vector molecule are capable of growing on this agar. Using this process, after incubation at 37° C., 6 resulting colonies were selected and the plasmids were isolated from them using the method of Birnboim et al. (see Nucl. Acids Res. 7, 1513 (1979)). After restriction enzyme digestion of the selected plasmids with EcoRI, HindIII, NcoI and PstI and subsequent gel electrophoresis, the correctness of the construction of these plasmids was confirmed. A plasmid thus obtained having the following restriction map

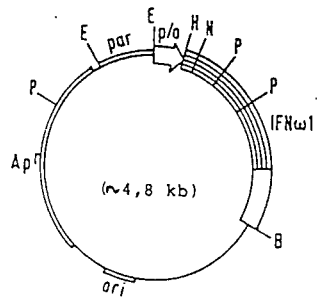

in which IFNω1 represents the DNA sequence coding for IFN-omegal(Gly) or IFN-omegal(Glu), was selected and designated pRHW14 (see FIG. 2) if the starting plasmid used is the plasmid pRHW12 which codes for omegaI(Gly) interferon. When transformed in E. coli HB101 this plasmid shows the phenotype Ap$^r$ and Tc$^s$.

If pRHW11 is used as the starting plasmid, the plasmid pRHW13 which codes for omegaI(Glu)-interferon is obtained analogously.

Figure 3:
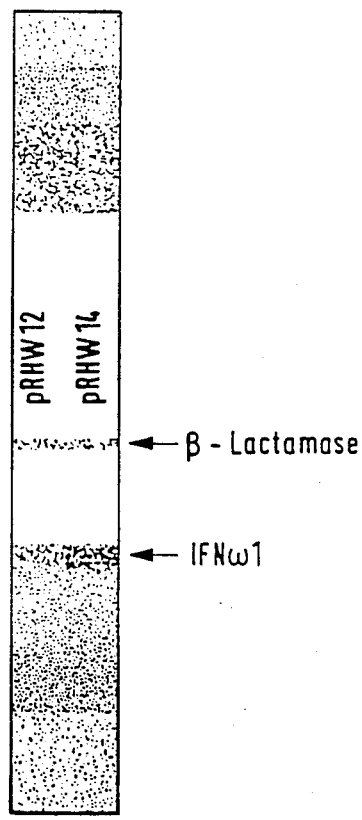
FIG. 3: autoradiograph of $^{35}$S labelled proteins from maxicells (*E. coli* CSR 603)

The plasmid pRHW14 thus obtained has twice as great an expression rate for the omegaI (Gly)-interferon as the plasmid pRHW12 known hitherto (see EP-A-No. 0.170.204), as can be demonstrated in the Maxicell system (see J. Bacteriol. 137, 692–693 (1979)). For this, E. coli CSR603 (genotype F$^-$, thr-1, leuB6, proA2, phr-1, recA1, argE3, thi-1, uvrA6, ara-14, lacY1, galK2, xyl-5, mtl-1, gyrA98 (nalA98), rpsL31, tsx-33, lambda$^-$, supE44), which is deficient in the repair system for UV induced damage, is transformed with the plasmids pRHW12 and pRHW14. If the radiation dosage is selected so that the bacterial chromosome is often damaged but the plasmids are hardly ever damaged, there is predominantly only transcription and consequently translation of plasmid-coded genes. If the medium contains $^{35}$S-methionine, mainly plasmid gene products are labelled which can be recorded directly with the aid of X-ray film, after separation on an acrylamide gel, using an intensifier film (see FIG. 3). The ampicillin resistance gene product ($\beta$-lactamase, bla) is labelled equally strongly in both cases. In the case of pRHW14, however, the omegaI (Gly)-interferon is labelled twice as strongly as in the case of pRHW12.

Figure 4:
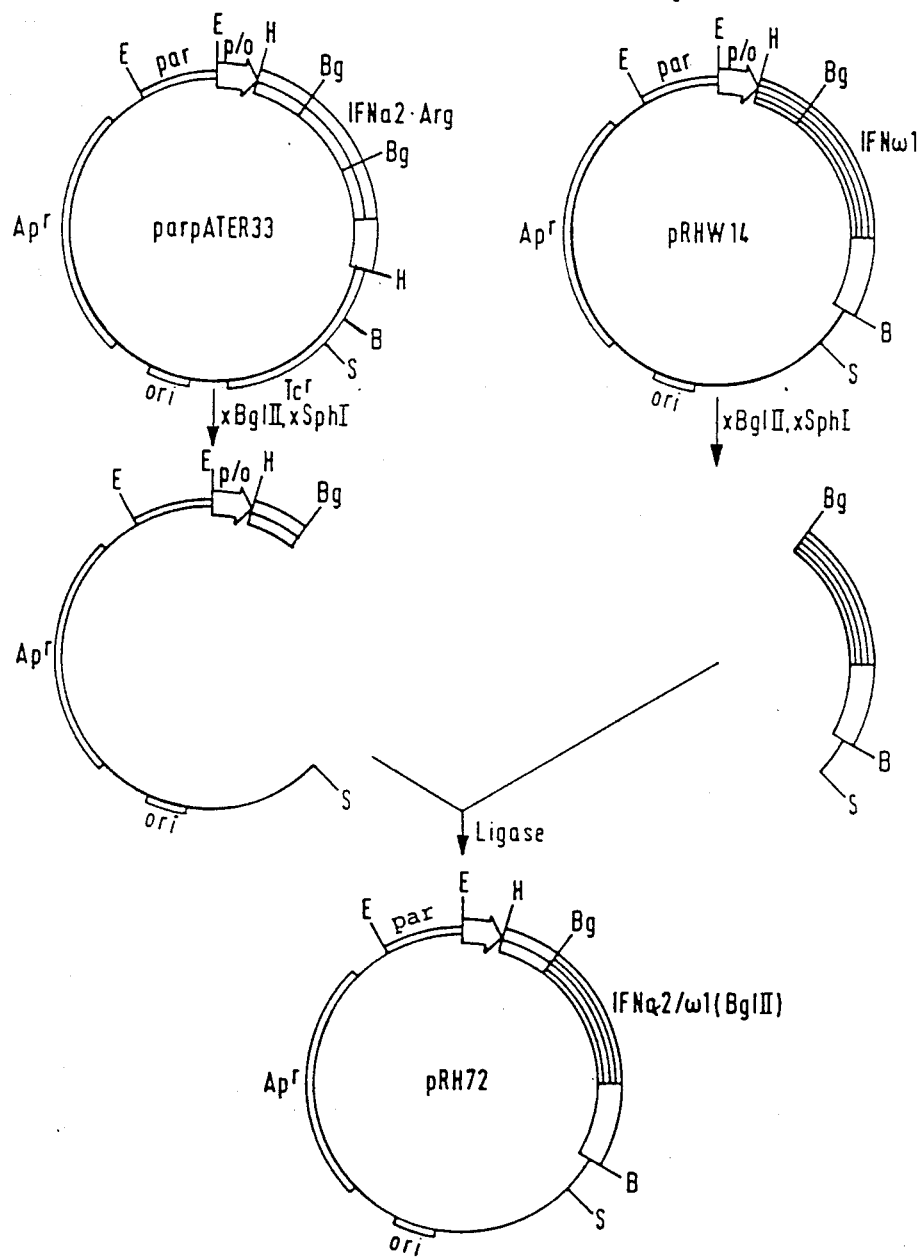
FIG. 4: construction scheme for pRH72

In order to prepare a plasmid which codes for a hybrid interferon of formula I and which contains the DNA sequences coding for $\alpha$1- or $\alpha$2-interferon before the common BglII cutting site (for the construction plan see FIG. 4), the plasmid parpATER33, for example, and a plasmid coding for an omegaI-interferon, such as the plasmid pRHW14, are each cut with BglII and SphI. The fragments thus produced are separated by gel electrophoresis, e.g. using 1% agarose gel, eluted and purified by ethanol precipitation. Starting with parpATER33 and pRHW14, after the fragments thus obtained had been dissolved in a suitable buffer, e.g. in TE buffer, the large fragment obtained from the plasmid parpATER33 was ligated with the smaller fragment obtained from the plasmid pRHW14 in the presence of a ligase, e.g. T$_4$ DNA-ligase. In order to replicate the plasmids obtained, bacteria, preferably E. coli of the HB101 strain (genotype F$^-$, hsdS20(r$^-$, m$^-$), recA13, ara-14, proA2, lacY1, galK2, rpsL20 (Sm$^r$), xyl-5, mtl-1, supE44, lambda$^-$), were washed with a CaCl$_2$ solution and the competent E. coli HB101 thus obtained were mixed with the ligase reaction mixture and after incubation at 0° C. the plasmid DNA was taken up by the bacteria by heat shock at 42° C. for 2 minutes. Subsequently, the transformed bacteria were placed onto LB agar containing ampicillin (LB medium+15 g/1 of agar).

Only E. coli HB101 bacteria which have taken up a recombinant vector molecule are capable of growing on this agar. After incubation at 37° C., several of the colonies which had formed were selected and the plasmids were isolated from them using the method of Birnboim et al. (see Nucl. Acids Res. 7, 1513 (1979)). By restriction enzyme double digestion of the selected plasmids with BglII and SphI and subsequent gel electrophoresis of the fragments obtained, the correctness of the construction of these plasmids was confirmed. A plasmid thus obtained was selected and designated pRH72. This plasmid having the following restriction map

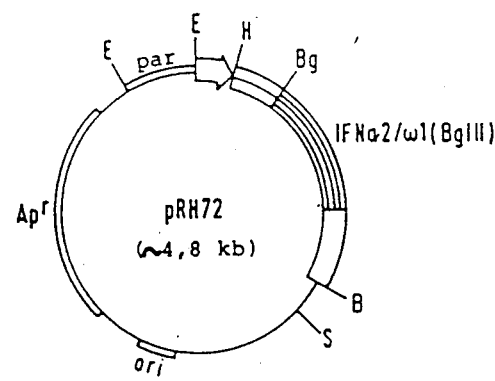

shows the phenotype Ap$^r$ and Tc$^s$ when transformed in E. coli HB101 and codes for the IFN-$\alpha$2/omegaI (Gly) (BglII) of formula

|  |  |  |  | 5 |  |  |  |  | 10 |  |  |  |  | 15 |
|---|---|---|---|---|---|---|---|---|---|---|---|---|---|---|
| Cys | Asp | Leu | Pro | Gln | Thr | His | Ser | Leu | Gly | Ser | Arg | Arg | Thr | Leu |
|  |  |  |  | 20 |  |  |  |  | 25 |  |  |  |  | 30 |
| Met | Leu | Leu | Ala | Gln | Met | Arg | Arg | Ile | Ser | Leu | Phe | Ser | Cys | Leu |
|  |  |  |  | 35 |  |  |  |  | 40 |  |  |  |  | 45 |
| Lys | Asp | Arg | Arg | Asp | Phe | Gly | Phe | Pro | Gln | Glu | Glu | Phe | Gly | Asn |
|  |  |  |  | 50 |  |  |  |  | 55 |  |  |  |  | 60 |
| Gln | Phe | Gln | Lys | Ala | Glu | Thr | Ile | Pro | Val | Leu | His | Glu | Met | Ile |
|  |  |  |  | 65 |  |  |  |  | 70 |  |  |  |  | 75 |
| Gln | Gln | Ile | Phe | Ser | Leu | Phe | His | Thr | Glu | Arg | Ser | Ser | Ala | Ala |
|  |  |  |  | 80 |  |  |  |  | 85 |  |  |  |  | 90 |
| Trp | Asn | Met | Thr | Leu | Leu | Asp | Gln | Leu | His | Thr | Gly | Leu | His | Gln |
|  |  |  |  | 95 |  |  |  |  | 100 |  |  |  |  | 105 |
| Gln | Leu | Gln | His | Leu | Glu | Thr | Cys | Leu | Leu | Gln | Val | Val | Gly | Glu |
|  |  |  |  | 110 |  |  |  |  | 115 |  |  |  |  | 120 |
| Gly | Glu | Ser | Ala | Gly | Ala | Ile | Ser | Ser | Pro | Ala | Leu | Thr | Leu | Arg |
|  |  |  |  | 125 |  |  |  |  | 130 |  |  |  |  | 135 |
| Arg | Tyr | Phe | Gln | Gly | Ile | Arg | Val | Tyr | Leu | Lys | Glu | Lys | Lys | Tyr |

|     |     |     |     | 140 |     |     |     |     | 145 |     |     |     |     | 150 |
| --- | --- | --- | --- | --- | --- | --- | --- | --- | --- | --- | --- | --- | --- | --- |
| Ser | Asp | Cys | Ala | Trp | Glu | Val | Val | Arg | Met | Glu | Ile | Met | Lys | Ser |
|     |     |     |     | 155 |     |     |     |     | 160 |     |     |     |     | 165 |
| Leu | Phe | Leu | ser | Thr | Asn | Met | Gln | Glu | Arg | Leu | Arg | Ser | Lys | Asp |
|     |     |     |     | 170 |     |
| Arg | Asp | Leu | Gly | Ser | Ser | the Met and N-formyl-Met derivatives thereof and the N-glycosylated derivative thereof, and contains the sequence of formula

```
ATG TGT GAT CTG CCT CAA ACC CAC AGC              15
    CTG GGT AGC AGG AGG ACC                      45

TTG ATG CTC CTG GCA CAG ATG AGG
    AGA ATC TCT CTT TTC TCC TGC                  90
                                                 20
TTG AAG GAC AGA CGT GAC TTT GGA
    TTT CCC CAG GAG GAG TTT GGC                 135

AAC CAG TTC CAA AAG GCT GAA ACC
    ATC CCT GTC CTC CAT GAG ATG                 180
                                                 25
ATC CAG CAG ATC TTC AGC CTC TTC CAC
    ACA GAG CGC TCC TCT GCT                     225

GCC TGG AAC ATG ACC CTC CTA GAC CAA
    CTC CAC ACT GGA CTT CAT                     270
                                                 30
CAG CAA CTG CAA CAC CTG GAG ACC
    TGC TTG CTG CAG GTA GTG GGA                 315

GAA GGA GAA TCT GCT GGG GCA ATT
    AGC AGC CCT GCA CTG ACC TTG                 360
                                                 35
AGG AGG TAC TTC CAG GGA ATC CGT
    GTC TAC CTG AAA GAG AAG AAA                 405

TAC AGC GAC TGT GCC TGG GAA GTT
    GTC AGA ATG GAA ATC ATG AAA                 450
                                                 40
TCC TTG TTC TTA TCA ACA AAC ATG CAA
    GAA AGA CTG AGA AGT AAA                     495

GAT AGA GAC CTG GGC TCA TCT TGA                 519
``` coding for this polypeptide. It should be understood that the IFN-α2/omegal (Gly) coding sequence of pRH72 may be substituted by degenerate variants thereof.

Figure 5:
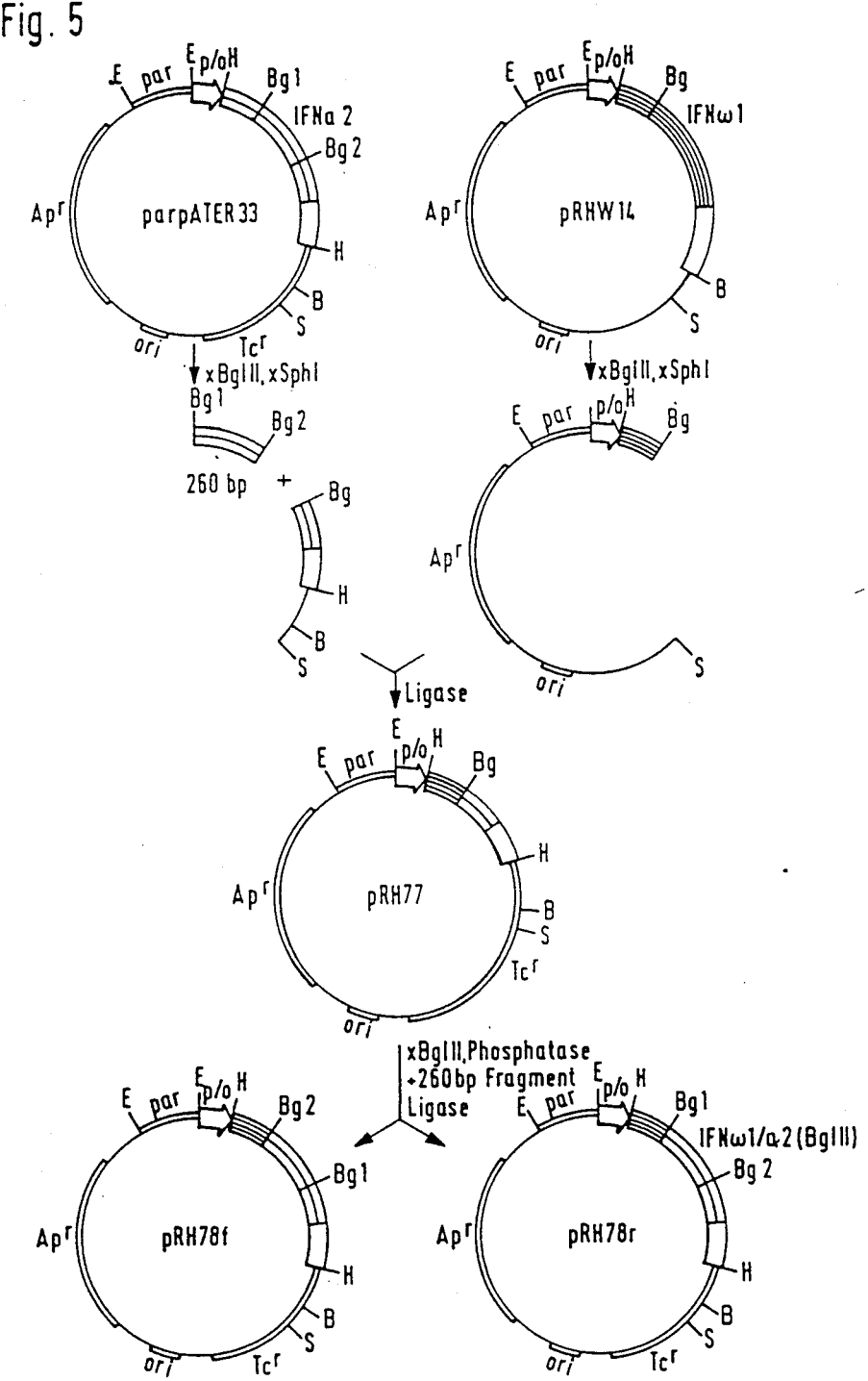
FIG. 5: construction scheme for pRH78r and pRH78f

In order to prepare a plasmid coding for a hybrid interferon of formula I and containing the DNA sequence coding for an omegal-interferon before the common BglII cutting site (for the construction plan see FIG. 5), a two-step procedure must be followed if there are two BglII cutting sites in the DNA sequence of the α-interferon, as in the DNA sequence of IFN-α2 (Arg).

In the first step, the large fragment obtained from the plasmid pRHW14 by cutting with BglII and SphI is ligated with the fragment obtained from the plasmid parpATER33 by digestion with BglII and SphI, which encodes the C terminus of IFN-α2 (Arg), in the presence of a ligase, e.g. T4 DNA ligase. In order to replicate the plasmids formed, bacteria, preferably E. coli HB101, are transformed and cultivated. The structures of selected plasmids are checked as described above with reference to the preparation of the plasmid pRH72.

A plasmid thus obtained was selected and designated pRH77 and has the following restriction map:

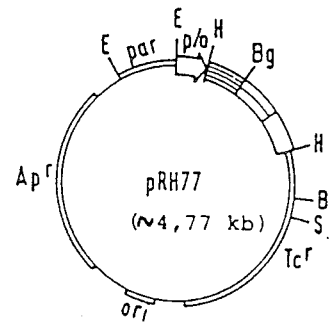

In the second step, in order to complete the gene for the hybrid interferon, e.g. the IFN-omegal/α2(BglII), the fragment comprising positions 192–455 which was removed during the cutting of parpATER33 must be re-inserted into the plasmid pRH77. To do this, the plasmid pRH77 is cut with BglII and the 5'-terminal phosphate is removed using calves' intestine phosphatase (CIP). The linearised form of the plasmid pRHW77 thus obtained is separated by gel electrophoresis, e.g. using a 1% agarose gel, isolated and purified by ethanol precipitation. After the linearised fragment thus obtained has been dissolved in a suitable buffer, e.g. in TE buffer, this fragment is ligated with the 263 bp fragment obtained during the original digestion of parpATER33 with BglII and SphI, in the presence of a ligase such as T4 DNA-ligase. In order to replicate the plasmids obtained, bacteria, preferably E. coli HB101, are transformed and cultivated as described hereinbefore with reference to the preparation of the plasmid pRH72. Selected plasmids are checked for the correctness of their structure by cutting with the restriction endonucleases AluI or HaeIII. On account of the identical ends, the 263 bp fragment may be inserted in two directions.

The plasmid in which the 263 bp BglII fragment is inserted in the correct position for expression, is designated pRH78r, whilst the plasmid with the wrong orientation for expression is designated pRH78f.

When transformed in E. coli HB101, both plasmids show the phenotype Ap$^r$ and Tc$^r$. The plasmid pRH78r having the following restriction map:

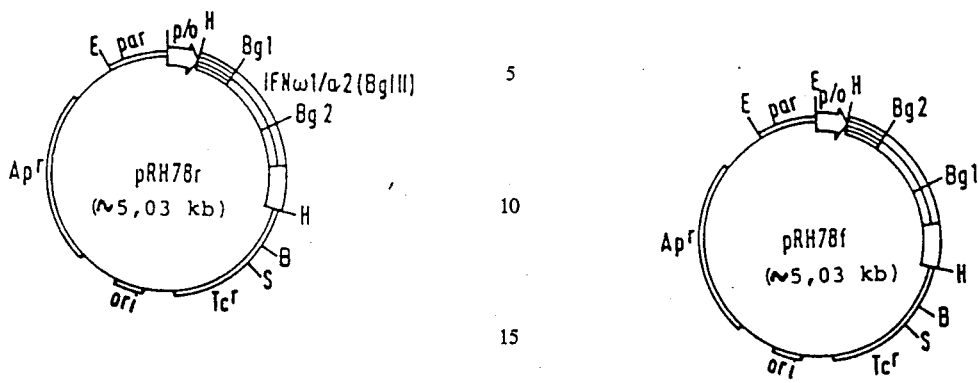

The plasmid pRH78f having the restriction map:

encodes the following polypeptide sequence for IFN-omegal/α2(BglII) and contains the below stated nucleotide sequence coding for this polypeptide:

encodes the following polypeptide sequence and contains the below stated nucleotide sequence coding for

| | | | | 5 | | | | | 10 | | | | | 15 | | |
|---|---|---|---|---|---|---|---|---|---|---|---|---|---|---|---|---|
| Met | Cys | Asp | Leu | Pro | Gln | Asn | His | Gly | Leu | Leu | Ser | Arg | Asn | Thr | | |
| ATG | TGT | GAT | CTG | CCT | CAG | AAC | CAT | GGC | CTA | CTT | AGC | AGG | AAC | ACC | | 45 |
| | | | | 20 | | | | | 25 | | | | | 30 | | |
| Leu | Val | Leu | Leu | His | Gln | Met | Arg | Arg | Ile | Ser | Pro | Phe | Leu | Cys | | |
| TTG | GTG | CTT | CTG | CAC | CAA | ATG | AGG | AGA | ATC | TCC | CCT | TTC | TTG | TGT | | 90 |
| | | | | 35 | | | | | 40 | | | | | 45 | | |
| Leu | Lys | Asp | Arg | Arg | Asp | Phe | Arg | Phe | Pro | Gln | Glu | Met | Val | Lys | | |
| CTC | AAG | GAC | AGA | AGA | GAC | TTC | AGG | TTC | CCC | CAG | GAG | ATG | GTA | AAA | | 135 |
| | | | | 50 | | | | | 55 | | | | | 60 | | |
| Gly | Ser | Gln | Leu | Gln | Lys | Ala | His | Val | Met | Ser | Val | Leu | His | Glu | | |
| GGG | AGC | CAG | TTG | CAG | AAG | GCC | CAT | GTC | ATG | TCT | GTC | CTC | CAT | GAG | | 180 |
| | | | | 65 | | | | | 70 | | | | | 75 | | |
| Met | Leu | Gln | Gln | Ile | Phe | Asn | Leu | Phe | Ser | Thr | Lys | Asp | Ser | Ser | | |
| ATG | CTG | CAG | CAG | ATC | TTC | AAT | CTC | TTC | AGC | ACA | AAG | GAC | TCA | TCT | | 225 |
| | | | | 80 | | | | | 85 | | | | | 90 | | |
| Ala | Ala | Trp | Asp | Glu | Thr | Leu | Leu | Asp | Lys | Phe | Tyr | Thr | Glu | Leu | | |
| GCT | GCT | TGG | GAT | GAG | ACC | CTC | CTA | GAC | AAA | TTC | TAC | ACT | GAA | CTC | | 270 |
| | | | | 95 | | | | | 100 | | | | | 105 | | |
| Tyr | Gln | Gln | Leu | Asn | Asp | Leu | Glu | Ala | Cys | Val | Ile | Gln | Gly | Val | | |
| TAC | CAG | CAG | CTG | AAT | GAC | CTG | GAA | GCC | TGT | GTG | ATA | CAG | GGG | GTG | | 315 |
| | | | | 110 | | | | | 115 | | | | | 120 | | |
| Gly | Val | Thr | Glu | Thr | Pro | Leu | Met | Lys | Glu | Asp | Ser | Ile | Leu | Ala | | |
| GGG | GTG | ACA | GAG | ACT | CCC | CTG | ATG | AAG | GAG | GAC | TCC | ATT | CTG | GCT | | 360 |
| | | | | 125 | | | | | 130 | | | | | 135 | | |
| Val | Arg | Lys | Tyr | Phe | Gln | Arg | Ile | Thr | Leu | Tyr | Leu | Lys | Glu | Lys | | |
| GTG | AGG | AAA | TAC | TTC | CAA | AGA | ATC | ACT | CTC | TAT | CTG | AAA | GAG | AAG | | 405 |
| | | | | 140 | | | | | 145 | | | | | 150 | | |
| Lys | Tyr | Ser | Pro | Cys | Ala | Trp | Glu | Val | Val | Arg | Ala | Glu | Ile | Met | | |
| AAA | TAC | AGC | CCT | TGT | GCC | TGG | GAG | GTT | GTC | AGA | GCA | GAA | ATC | ATG | | 450 |
| | | | | 155 | | | | | 160 | | | | | 165 | | |
| Arg | Ser | Phe | Ser | Leu | Ser | Thr | Asn | Leu | Gln | Glu | Ser | Leu | Arg | Ser | | |
| AGA | TCT | TTT | TCT | TTG | TCA | ACA | AAC | TTG | CAA | GAA | AGT | TTA | AGA | AGT | | 495 |
| Lys | Glu | | | | | | | | | | | | | | | |
| AAG | GAA | TGA | | | | | | | | | | | | | | 504 | this polypeptide:

| | | | | 5 | | | | | 10 | | | | | 15 | | |
|---|---|---|---|---|---|---|---|---|---|---|---|---|---|---|---|---|
| Met | Cys | Asp | Leu | Pro | Gln | Asn | His | Gly | Leu | Leu | Ser | Arg | Asn | Thr | | |
| ATG | TGT | GAT | CTG | CCT | CAG | AAC | CAT | GGC | CTA | CTT | AGC | AGG | AAC | ACC | | 45 |

-continued

| | | | | 20 | | | | | 25 | | | | | 30 | |
|---|---|---|---|---|---|---|---|---|---|---|---|---|---|---|---|
| Leu | Val | Leu | Leu | His | Gln | Met | Arg | Arg | Ile | Ser | Pro | Phe | Leu | Cys | |
| TTG | GTG | CTT | CTG | CAC | CAA | ATG | AGG | AGA | ATC | TCC | CCT | TTC | TTG | TGT | 90 |
| | | | | 35 | | | | | 40 | | | | 45 | | |
| Leu | Lys | Asp | Arg | Arg | Asp | Phe | Arg | Phe | Pro | Gln | Glu | Met | Val | Lys | |
| CTC | AAG | GAC | AGA | AGA | GAC | TTC | AGG | TTC | CCC | CAG | GAG | ATG | GTA | AAA | 135 |
| | | | | 50 | | | | | 55 | | | | | 60 | |
| Gly | Ser | Gln | Leu | Gln | Lys | Ala | His | Val | Met | Ser | Val | Leu | His | Glu | |
| GGG | AGC | CAG | TTG | CAG | AAG | GCC | CAT | GTC | ATG | TCT | GTC | CTC | CAT | GAG | 180 |
| | | | | 65 | | | | | | | | | | | |
| Met | Leu | Gln | Gln | Ile | Ser | | | | | | | | | | |
| ATG | CTG | CAG | CAG | ATC | TCA | TGA | TTT | CTG | CTC | TGA | CAA | CCT | CCC | AGG | 225 |
| CAC | AAG | GGC | TGT | ATT | TCT | TCT | CTT | TCA | GAT | AGA | GAG | TGA | TTC | TTT | 270 |
| GGA | AGT | ATT | TCC | TCA | CAG | CCA | GAA | TGG | AGT | CCT | CCT | TCA | TCA | GGG | 315 |
| GAG | TCT | CTG | TCA | CCC | CCA | CCC | CCT | GTA | TCA | CAC | AGG | CTT | CCA | GGT | 360 |
| CAT | TCA | GCT | GCT | GGT | AGA | GTT | CAG | TGT | AGA | ATT | TGT | CTA | GGA | GGG | 405 |
| TCT | CAT | CCC | AAG | CAG | CAG | ATG | AGT | CCT | TTG | TGC | TGA | AGA | GAT | TGA | 450 |
| AGA | TCT | TTT | TCT | TTG | TCA | ACA | AAC | TTG | CAA | GAA | AGT | TTA | AGA | AGT | 505 |
| AAG | GAA | TGA | | | | | | | | | | | | | 514 |

For the purposes of replication or expression, the new plasmids according to this invention may be introduced into a bacterial host. Prokaryotes such as *E. coli* K12, strain 294 (ATCC No. 31.446), *E. coli* X1776 (ATCC No. 31.537), *E. coli* W3110 (F−, lambda−, protographic, ATCC No. 27.325), *E. coli* HB101 ((F−, hsdS20(r−, m−), recA13, ara-14, proA2, lacY1, galK2, rpsL20(Smr), xyl-5, mtl-1, supE44, lambda−), Bacilli such as *Bacillus subtilis*, and other Enterobacteriaceae, such as *Salmonella typhimurium* or *Serratia marcescens* and various Pseudomonads have proved suitable.

In order to express the new hybrid interferon, the plasmids pRH72, pRH78f and pRH78r, for example, were transformed in *E. coli* and cultivated. The antiviral activity of the polypeptides expressed was determined in the cell residues after destruction of the cell walls and removal of the bacterial debris by centrifuging, using the CPE reduction test. It was found that the cell residues obtained from *E. coli* transformed with pRH72 and *E. coli* transformed with pRH78f showed no antiviral properties. Surprisingly, however, the cell residue obtained from the plasmid pRH78r, which contains IFN-omegal/α2(BglII), has a specific antiviral activity on A549 cells which is about four times greater than that of IFN-α2(Arg).

The DNA sequences of the new plasmids produced according to the invention coding for a new hybrid interferon may, furthermore, be introduced into any other organism after suitable modification.

The expression and translation of a sequence of this kind may also be carried out under the control of other regulating systems which may be regarded as "homologous" to the organism in its untransformed form. Thus, for example, chromosomal DNA from a lactose-dependent *E. coli* contains a lactose or lac-operon which makes lactose degradation possible by directing expression of the enzyme β-galactosidase.

The lac control elements may be obtained from the bacteriophage lambda-plac5, which is infectious to *E. coli*. The lac-operon of the phage may be obtained from the same bacterial species by transduction. Regulating systems which may be used in the process according to the invention may also originate from plasmid DNA native to the organism. The lac-promoter/operator system may be induced by IPTG (isopropylthiogalactoside).

Other promoter/operator systems or parts thereof may be used with equal success: for example, the arabinose promoter/operator, the colicin $E_1$ promoter/operator, the galactose promoter/operator, the alkaline phosphatase promoter/operator, the trp promoter/operator, the xylose-A promoter/operator, the tac promoter, etc.

In addition to prokaryotes, it is also possible to use eukaryotes such as yeast. *Saccharomyces cerevisiae* is the most commonly used of the eukaryotic microorganisms, although a number of other species are generally available. For expression in *Saccharomyces*, the plasmid YRp7, for example (Stinchcomb et al. Nature 282, 39 (1979); Kingsman et al., Gene 7, 141 (1979); Tschumper et al., Gene 10, 157 (1980)) and the plasmid YEp 13 (Bwach et al., Gene 8, 121–133 (1979)) are normally used. The plasmid YRp7 contains the TRP1 gene, which provides a selection marker for a yeast mutant which is incapable of growing in tryptophanfree medium; for example ATCC No. 44076.

The presence of the TRP1 mutation as a characteristic of the yeast host genome represents an effective tool for demonstrating transformation, cultivation being carried out without tryptophan. The situation is just the same with the plasmid YEp13, which contains the yeast gene LEU 2, which can be used to supplement a LEU-2-minus mutant. Suitable promoter sequences for yeast vectors contain a 5'-flanking region of the genes of ADH I (Ammerer G., Methods of Enzymology 101, 192–201 (1983)), 3-phosphoglycerate-kinase (Hitzeman et al., J. Biol. Chem. 255, 2073 (1980)) or other glycolytic enzymes (Kawaski and Fraenkel, BBRC 108, 1107–1112 (1982)) such as enolase, glyceraldehyde-3-phosphate-dehydrogenase, hexokinase, pyruvate decarboxylase, phosphofructokinase, glucose-6-phosphate isomerase, phosphoglucose isomerase and glucokinase. When constructing suitable expression plasmids, the terminal sequences associated with these genes may also be inserted in the expression vector at the 3' end of the sequence which is to be expressed, in order to provide polyadenylation and termination of the mRNA.

Other promoters which also have the advantage of transcription controlled by the growth conditions include the promoter regions of the genes for alcohol dehydrogenase-2, isocytochrome C, acid phosphatase, degrading enzymes which are associated with nitrogen metabolism, the above-mentioned glyceraldehyde-3-phosphate dehydrogenase and enzymes which are responsible for the processing of maltose and galactose. Promoters which are regulated by the yeast mating type locus, for example promoters of the genes BARI, MFα1, STE2, STE3 and STE5, may be inserted in temperature-regulated systems by using temperature-dependent sir mutations. (Rhine PH.D. in Thesis, University of Oregon, Eugene, Oreg. (1979), Herskowitz and Oshima, The Molecular Biology of the Yeast *Saccharomyces*, part I, 181-209 (1981), Cold Spring Harbor Laboratory). These mutations affect expression of the resting mating type cassettes of yeasts and hence, indirectly, the mating type-dependent promoters. Generally, however, any vector which contains a yeast-compatible promoter and yeast-specific replication and termination sequences is suitable.

In addition to microorganisms, cultures of multicellular organisms are also suitable host organisms. Theoretically, any of these cultures may be used, from either vertebrate or invertebrate cell cultures. However, the greatest interest has been shown in vertebrate cells, with the result that the multiplying of vertebrate cells in culture (tissue culture) has become a routine procedure in recent years (Tissue Culture, Academic Press, Kruse and Patterson, Editors (1973)). Examples of useful host cell lines of this kind include VERO and HeLa cells, chinese hamster ovary (CHO) cells and W138, BHK, COS-7 and MDCK cell lines. Expression vectors for these cells generally contain a replication origin, a promoter which is located in front of the gene to be expressed, together with the necessary RNA splicing site, polyadenylation site and transcription termination sequences.

When used in mammalian cells, the control functions on the expression vectors are frequently taken from viral material. For example, the promoters conventionally used are obtained from Polyoma Adenovirus 2 and, particularly frequently, from Simian Virus 40 (SV 40). The promoters of the early and late genes of SV 40 are particularly useful, since they are both easily obtained from the virus as a fragment which still contains the viral replication origin of SV 40. (Fiers et al., Nature 273, 113 (1978)). It is also possible to use smaller or larger fragments of SV 40, provided that they contain the sequence, approximately 250 bp long, which extends from the HindIII cutting site to the Bgl 1 cutting site in the viral replication site. Moreover, it is also possible and often advisable to use promoter or control sequences which are normally connected with the desired genetic sequences, provided that these control sequences are compatible with the host cell systems.

A replication site may either be provided by suitable vector construction in order to incorporate an exogenic site, for example from SV 40 or other viral sources (e.g. Polyoma, Adeno, VSV, PBV, etc.) or it may be provided by the chromosomal replication mechanisms of the host cell. If the vector is integrated into the host cell chromosome, the latter procedure is generally sufficient.

On the basis of their biological activity spectrum the new hybrids according to the invention, particularly IFN-omegal/α2(BglII) interferon, may be used for any type of treatment for which the known interferons are used. These include, for example, Herpes virus, Rhinovirus, viral infections in AIDS and other viral diseases, various types of cancer and the like. The new interferons may be used on their own or in conjunction with other known interferons or biologically active products, for example with IFN-γ, IL-2, other immune modulators and the like.

An IFN-omega/α hybrid such as IFN-omegal/α2(BglII) may be administered by the parenteral route in cases in which antitumour or antiviral treatment is required, and for antiviral prophylaxis in immune-suppressed patients. The dosage and dosage rate may be similar to those currently used in clinical trials for IFN-α materials, e.g. about $(1-10) \times 10^6$ units per day and, in preparations which are more than 1% pure, up to about $5 \times 10^7$ units daily.

For example, to produce a convenient dosage form for a substantially homogeneous bacterially produced IFN-omegal/α2(BglII), for parenteral use 3 mg of IFN-omegal/α2(BglII) may be dissolved in 25 ml of 5% human serum albumin. This solution is then passed through a bacteriological filter and the filtered solution is distributed between 100 vials under aseptic conditions, each vial containing $6 \times 10^6$ units of pure IFN-omegal/α2(BglII) suitable for parenteral administration. The glass vials are preferably stored under cool conditions ($-20°$ C.) before use. The substances according to the invention may be formulated in known manner in order to obtain pharmaceutically usable compositions, the polypeptide according to the invention being mixed with a pharmaceutically acceptable carrier substance. Conventional carriers and their formulations are described by E. W. Martin in Remington's Pharmaceutical Sciences, to which reference is expressly made. IFN-omegal/α2(BglII) is mixed with a suitable quantity of the carrier in order to produce suitable pharmaceutical preparations which can be effectively administered to the patient. Parenteral administration is preferred.

Moreover, the new hybrid interferons are suitable for preparing antibodies against these interferons, particularly IFN-omegal/α2(BglII), which simultaneously also recognise the parental interferons IFN-α2 and IFN-omegal. The antibodies thus produced are therefore suitable for immune affinity chromatography of omega-interferons.

Thus, this application further relates to new monoclonal antibody-producing hybrid cell lines, processes for preparing them and a process for preparing monoclonal antibodies from mice which are specific to IFN-α and omega interferon, particularly omegal interferon.

The new monoclonal antibodies are therefore particularly suitable for high purification and for detecting omegal(Glu) or omegal(Gly) interferon.

The antibody-producing hybrid cell lines required for this are obtained by cell fusion of spleen cells from mice immunised with a hybrid interferon such as IFN-omegal/α2(Bg 1II), with myeloma cells, e.g. myeloma cells of the line P3-X-63Ag8-653 (see Nature 266, 550-552 (1977)). A cell line thus obtained secretes large quantities of an antibody which is capable of neutralising the antiviral activity both of the hybrid interferon used for immunisation and also of the two parental interferons, e.g., in the case IFN-omegal/α2(BglII), that of the omegal interferon and of the IFN-α2(Arg), and is suitable for affinity chromatography of omegal interferon.

After covalent bonding to a biologically inactive carrier, the antibody thus produced may be used for the ultra-purification of omegal interferons or IFN-α2.

The antibody is covalently bonded to a correspondingly activated carrier, preferably based on dextran, for example to CNBr-activated sepharose or CH-activated sepharose produced by the firm Pharmacia of Uppsala. For ultra-purification, a solution of the omegal interferon to be purified, which is appropriately obtained either by the process described in EP-A-0.170.204 or according to the invention using the new plasmids described hereinbefore, is pumped over an antibody affinity carrier thus produced, at a weakly basic pH, for example at a pH of 7 to 8 but preferably at pH 7.5, and washed at pH 7.5 until the eluate is free from protein, and subsequently the bound interferon is eluted in the acid range, e.g. using 0.1 M citric acid in 25% ethylene glycol. The protein-containing fractions thus obtained are then chromatographed over a strongly acidic cation exchanger, e.g. the cation exchanger Mono-S made by Pharmacia. The human interferon of the above eluate is immediately adsorbed by the cation exchanger column and subsequently eluted using an NaCl gradient.

The basic plasmids required in connection with this application were deposited at the Deutsche Sammlung für Mikroorganismen in the matter of EP-A-0,115,613 and EP-A-0,170,204, respectively, for example pER103 was deposited under DMS No. 2773 on 20th Dec. 1983, E76E9 was deposited under DMS No. 3003 and P9A2 was deposited under DMS No. 3004 on 4th Jul. 1984, and the necessary declaration of release has already been given for these clones. Using these plasmids, the person skilled in this art is readily able to reproduce the present invention with the aid of EP-A-0,115,613 and EP-A-0,170,204 (see also Nucleic Acids Res. 13, 4739–4749 (1985)).

The Examples which follow are intended to illustrate the invention without restricting it:

EXAMPLES

Preliminary remark

All enzyme reactions are carried out under the conditions specified by the manufacturer.

EXAMPLE 1

Preparation of parpATER33

10μg of parpER33 are cut in 200 μl of reaction solution with 20 units each of BamHI and PstI. Then the two fragments formed are separated in a 1% agarose gel (1% agarose in 1×TBE buffer: 10.8 g/l of Tris(hydroxymethyl)aminomethane (Tris), 5.5 g/l of boric acid, 0.93 g/l of ethylenediaminetetraacetic acid disodium salt (EDTA) and 0.5 mg/l of ethidium bromide (EtBr), the eluant buffer is 1×TBE; electrophoresis at 5V/cm; the DNA fragments are made visible by irradiating the agarose gel with UV light (254 nm)). The smaller fragment containing the interferon α2-Arg (IFN-α2(Arg)) is isolated (electrophoresis of the DNA band on DE-81 paper (Whatman), washing the paper with 200 mM NaCl, 25 mM Tris pH=7.5, 1 mM EDTA and eluting the DNA with 1 M NaCl, 25 mM Tris, pH=7.5, 1 mM EDTA) and the DNA is precipitated by adding 2.5 vols of ethanol. After centrifuging, the DNA is dried and taken up in a suitable volume of TE buffer (10 mM Tris pH=8.0, 1 mM EDTA).

10 μg of pAT153 are also cut with 20 units of BamHI and PstI in 200 μl reaction solution and the fragments obtained are separated. The larger fragment containing the replication origin is isolated from paT153.

0.5 μg of the purified DNA fragments are ligated in 20 μl of reaction solution (66 mM Tris, pH=7.5, 100 mM NaCl, 10 mM MgCl$_2$, 5 mM dithiothreitol (DTT), 1 mN EDTA, 1 mM adenosine triphosphate (ATP)) with 5 units of T$_4$ DNA ligase. Then 150 μl of competent E. coli HB101 bacteria (F$^-$, hsdS20(r$^-$, m$^-$), recA13, ara-14, proA2, lacY1, galK2, rpsL20(Smr), syl-5, mtl-1, supE44, lambda$^-$) are mixed with 1 μl of the ligase reaction mixture, incubated at 0° C. for 30 minutes and transformed by incubation for 2 minutes at 42° C. with the DNA (competent E. coli bacteria: E. coli is allowed to grow in LB medium (10 g/l trypton, 5 g/l yeast extract, 5 g/l NaCl, pH=7.5) up to OD$_{600nm}$=0.3 and centrifuged. The bacteria are resuspended in 0.5 vol of ice cold 50 mM CaCl$_2$ solution and incubated for 30 minutes. After being centrifuged again the bacteria are resuspended in 1/15 vol of the initial volume of 50 mM CaCl$_2$). The bacterial suspension is plated on LB agar (LB medium plus 15 of agar) with 50 μg/ml of ampicillin. After 16 hours' incubation at 37° C., 12 of the colonies thus formed were selected and from these the plasmids were isolated on a microscopic scale (Birnboim, H. C. and Doly, J., Nucl. Acids Res. 7, 1513 (1979)). The correctness of the construction was confirmed by restriction enzyme double digestion with PstI-BamHI, PstI-PvuII and EcoRI-BsmHI and with subsequent gel electrophoresis by the occurrence of the expected fragments. One plasmid was selected and designated parpATER33. E. coli transformed with parpATER33 shows the phenotype Ap$^r$ (ampicillin resistance), Tc$^r$ (tetracycline resistance).

EXAMPLE 2

Preparation of pRHW14

10 μg of parpATER33 are doubly digested in 150 μl of reaction solution with HindIII and BamHI. The three resulting DNA fragments are separated on 1% agarose gel and the largest fragment which is about 3750 base pairs (bp) long is isolated (fragment a). This fragment carries the tryptophan promoter/operator (Serratia marcescens), the replication orgin and the Ap$^r$ gene. 10 μg of pRHW12 are also doubly digested in 150 μl of reaction solution with BamHI and HindIII. The two fragments produced are separated by gel electophoresis and the smaller fragment, about 800 bp long, containing the IFN-omegal(Gly) gene is isolated (fragment b). 40 ng of fragment (a) are ligated with about 50 ng of fragment (b) in 10 μl of reaction solution with 5 units of T$_4$ DNA ligase. 200 μl of competent E. coli HB101 suspension are mixed with the ligase reaction solution, the bacteria are transformed by heat shock at 42° C. and plated on LB agar with 50 μl/ml of ampicillin. After 16 hours' incubation at 37° C., six colonies thus obtained were selected and the plasmid DNA was isolated from the bacteria on a microscopic scale. After the DNA had been digested with the restriction endonucleases EcoRI, HindIII, NcoI and PstI and after subsequent analysis of the fragments by gel electrophoresis, it was found that one of the plasmids had the desired structure. This plasmid was designated pRHW14. E. coli transformed with pRHW14 shows the phenotype Ap$^r$ and Tc$^s$.

EXAMPLE 3

Detection of the plasmid-coded proteins

Plasmid-coded proteins can be detected using the Maxicell system (Sancar. A., Hack, A. M. and Rupp, W. D., J. Bacteriol. 137, 692–693 (1979)). For this purpose, E. coli CSR603 (F$^-$, thr-1, leuB6, proA2, phr-1, recA1, argE3, thi-1, uvrA6, ara-14, lacY1, galK2, xyl-5, mtl-1, gyrA98, (nalA98), rpsL31, tsx-33, lambda$^-$, supE44, transformed with the plasmids pRHW12 and pRHW14, is grown in the expression medium (10 g/l (NH$_4$)$_2$PO$_4$, 3.5 g/l KH$_2$PO$_4$, PH=7.3, 0.5 g/l NaCl, 21 g/l, casein hydrolysate (acid-hydrolysed, vitamin-free), 11 g/l of glucose, 1 mM MgSO$_4$, 0.1 mM CaCl$_2$, 1 mg/l thiamine-HCl, 20 mg/l L-cysteine, 100 mg/l ampicillin) up to a density of OD$_{600nm}$=0.6 at 37° C. 10 ml of culture are irradiated in an open Petri dish with a UV germicidal lamp (15 W) for 5 seconds from a distance of 50 cm and incubated for a further hour. 100 μg of D-cycloserine are added to the cultures in order to kill off any bacteria still capable of multiplying. After 16 hours' incubation at 37° C., the bacteria are centrifuged, washed twice with 5 ml of Hershey salt solution (5.4 g/l NaCl, 3.0 g/l KCl, 1.1 g/l NH$_4$Cl, 15 mg/l CaCl$_2$×2H$_2$O, 0.2 g/l MgCl$_2$×6H$_2$O, 0.2 mg/l FeCl$_3$×6H$_2$O, 87 mg/l KH$_2$PO$_4$, 12.1 g/l Tris pH=7.4), and incubated in 5 ml of Hershey medium (containing, per 100 ml of Hershey salts: 2.0 ml of 20% glucose, 0.5 ml of 2% threonine, 1.0 ml of 1% leucine, 1.0 ml of 2% proline, 2% arginine, 0.1 ml of 0.1% thiamineHCL) together with 20 μg/ml of indolacrylic acid (IAA). By adding 5 μCi/ml of $^{35}$S-methionine and incubating for a further hour at 37° C., newly synthesised proteins are radioactively labelled. The bacteria are centrifuged and lysed for 5 minutes at 100° C. in 200 μl of Na-dodecylsulphate (SDS) sample buffer (6.6 mM Na phosphate pH=6.8, 2 mM EDTA, 2% SDS, 3% glycerol, 0.02% bromophenol blue and 0.66% 2-mercaptoethanol). The samples are then separated in a 15% polyacrylamide gel (separating gel: 15% acrylamide, 0.4% bisacrylamide, 375 mM Tris pH=8.8, 2 mM EDTA, 0.1% SDS; collecting gel: 6% acrylamide, 0.16% bisacrylamide, 375 mM Tris pH=6.8, 2 mM EDTA, 0.1% SDS; electrode buffer: 3.0 g/l Tris, 14.2 g/l glycine, 0.335 g/l EDTA, 0.5 g/l DSD; duration of electrophoresis: 16 hours at a constant 20 mA). The gel is fixed for one hour in 20% methanol, 7.5% acetic acid, incubated for 30 minutes in 5% methanol, 1% glycerol and dried in a gel drier. The gel is exposed at −80° C. on Kodak X Omat S X-ray film using an intensifier field (Kodak). The ampicillin-resistant gene product (β-lactamase) is labelled equally strongly in both cases. However, when pRHW14 is used, IFN-omegal is labelled more than twice as strong as when pRHW12 is used (see Figure 3).

EXAMPLE 4

Extraction of IFN-omegal (Gly) from bacteria

E. coli HB101 transformed with pRHW12 or pRHW14 is grown in the expression medium together with 20 μg/ml of IAA up to OD$_{600nm}$=20. The bacteria are killed off by adding H$_2$SO$_4$ until a pH of 2 is attained and incubated for 60 minutes at 20° C. The bacteria are removed by centrifuging and the biomass is frozen at −20° C. until ready for working up. The bacteria are resuspended in 10 vol of 1% acetic acid. The pH of the solution is adjusted to 10 by the addition of 2 N NaOH and the suspension is stirred for 2 hours at 0° C. Then a pH of 7.5 is re-established with 2 N HCl and the cell debris is removed by centrifuging (J2-21 centrifuge (Beckman), JA10 rotor, 4° C., 10,000 rpm, 30 minutes). The interferon activity in the supernatant (crude extract) is measured by the Cytopathic Effect (CPE) reduction test on human A549 cells (human lung cancer cell line), infected with Encephalomyocarditis (EMC) virus, using IFN-α2(Arg) as standard. The biomass of E. coli tranformed with pRHW12 yields 100,000 units/gram (average of 3 independent cultures), whereas the clone pRHW14 yields 200,000 units/gram biomass (15 cultures).

EXAMPLE 5

Construction of the hybrid interferon expression clone pRH 72

10 μg of parpATER33 and pRHW14 are each doubly digested in 100 μl of solution with BglII and SphI. The fragments obtained are separated on 0.8% agarose gel and the DNAs are eluted and purified by precipitation. The fragments are dissolved in 20 μl of TE. The expression plasmid for IFN-α2/omegal (BglII) is prepared by ligase reaction of 1 μl large fragment of parpATER33 with 5 μl of small fragment of pRHW14 in a total of 20 μl, using 5 units of T$_4$ DNA ligase. After the transformation of E. coli HB101, the plasmids of some of the resulting ampicillin resistant clones are isolated on a microscopic scale and the correctness of the construction is checked by double restriction enzyme digestion using BglII/SphI. One of the plasmids thus selected has been designated pRH72. E. coli transformed with this plasmid has the phenotype Ap$^r$, Tc$^s$.

EXAMPLE 6

Construction of the plasmids pRH78r and pRH78f

1 μl of the large fragment of pRHW14 is ligated with 5 μl of the BglII(2)-SphI fragment from parpATER33, which encodes the C-terminus of IFN-α2(Arg), in 20 μl of reaction solution using 5 units of T$_4$ DNA ligase. E. coli HB101 is transformed with the resulting plasmid and, as described in Example 5, a plasmid of the desired construction is selected. This intermediate plasmid is designated pRH77. In order to complete the gene for the hybrid interferon omegal/α2(BglII), the fragment removed when parpATER33 is cut with BglII must be introduced into pRH77. To do this, 10 μg of pRH77 in 50 μl of solution are cut with BglII, the volume of the solution is doubled with 2×CIP buffer (CIP: calves intestine phosphatase, 2×CIP buffer: 100 mM Tris pH=9.0, 2 mM MgCl$_2$, 0.2 mM ZnCl$_2$), and the 5'-terminal phosphate is removed by the addition of one unit of CIP (Boehringer Mannheim) (60 minutes at 37° C.). The linearised form of pRH77 is purified by agarose gel electrophoresis and elution of the DNA with subsequent precipitation. The DNA is taken up in 20 μl of TE buffer and 1 μl thereof is ligated with 5 μl of the 263 bp fragment (BglII(1)-BglII(2) fragment), which is obtained when parpATER33 is digested with BglII/SphI, in a total of 10 μl of reaction solution with 5 units of T$_4$ DNA ligase. E. coli HB101 is transformed. DNA from six colonies thus formed was analysed. Since the insertion of the 263 bp fragment may take place in two directions, owing to the identical ends, the plasmids were checked for correct structure with the restriction endonucleoases AluI and HaeIII. The plasmid in which the BglII fragment had been inserted in the correct position for expression was designated pRHW78r, whilst the one with the wrong orientation for expression was designated pRH78f. E. coli transformed with pRH78r or pRH78f shows the phenotype Ap$^r$, Tc$^r$.

EXAMPLE 7

Lysate test for determining interferon (antiviral) activity

E. coli tramsformed with the various plasmids is grown in 35 ml of expression medium together with 20

μg/ul of IAA at 37° C. up to an $OD_{600nm}=0.6$. The bacteria are centrifuged. The bacterial pellet is taken up in 3.5 ml of 50 mM Tris pH=7.6/30 mM $MgCl_2$ solution and bombarded with an ultrasound disintegrator (MSE, Soniprep 150) at maximum power, whilst cooling with ice. The suspension is centrifuged for 10 minutes (J2-21 centrifuge, 10,000 rpm 4° C., JA20 rotor) and the supernatant is filtered under sterile conditions. The antiviral activity of the solution is determined by the CPE reduction test (A549 cells, EMC virus). E. coli transformed with pRH72 (IFN-α2/omegal(BglII)) does not yield any antiviral activity, for does E. coli transformed with pRH78f, which codes the first 64 amino acids of mature IFN-omegal followed by a serine. By contrast, the IFN-omegal/α2(BglII) coding sequence within the clone pRH78r produces about $30 \times 10^6$ units of interferon (compared with IFN-α2(Arg) as standard) per liter of culture and per 1 $OD_{600}$ nm bacterial density, which is a specific antiviral activity on A549 cells spproximately four times greater than that of IFN-α2(Arg).

The following Table lists the changes in the amino acids of the hybrid interferon IFN-omegal/α2(BglII) compared with IFN-α2(Arg):

| Position | IFN-α2(Arg) | IFN-omegal/α2 | Transition |
|---|---|---|---|
| 7 | Thr | Asn | p >> p |
| 9 | Ser | Gly | p >> p |
| 11 | Gly | Leu | p >> l |
| 14 | Arg | Asn | b >> p |
| 17 | Met | Val | (l) >> l |
| 20 | Ala | His | l >> b |
| 27 | Leu | Pro | l >> l |
| 29 | Ser | Leu | p >> l |
| 38 | Gly | Arg | p >> b |
| 43 | Glu | Met | a >> (l) |
| 44 | Phe | Val | ar >> l |
| 45 | O | Lys | O >> b |
| 47 | Asn | Ser | p >> p |
| 49 | Phe | Leu | ar >> l |
| 53 | Glu | His | a >> b |
| 54 | Thr | Val | p >> l |
| 55 | Ile | Met | l >> (l) |
| 56 | Pro | Ser | l >> p |
| 62 | Ile | Leu | l >> l |

Legend:
a: acid, ar; aromatic, b: basic, l; apolar, p: polar 0: no amino acid at this position Differences in the charges (position):
(1) Loss of 1 positive charge; 14
(2) Gain of 4 positive charges: 20, 38, 45, 53
(3) Loss of 2 negative charges: 43, 53

The hybrid has 5 more positive charges than IFN-α2(Arg).

EXAMPLE 9

Purification of IFN-omegal/α2(BglII)

145 g of acid-treated E. coli of the clone HB101/pRH 78r, frozen at −20° C., are stirred in 1450 ml of 1% acetic acid, whilst cooling with ice, until the material is evenly distributed (about 30 minutes) and then homogenised for $2\times 1$ minute using an Ultra-Turrax T 45/6 (Janke and Kunkel) at 10,000 rpm. Then Polymin P (Serva, Catalogue No. 33141) is added up to a concentration of 0.25% and the pH is adjusted to 10.0 using 5 N NaOH. After 2 hours' stirring whilst cooling with ice, the pH is adjusted to 7.5 using 5 N HCl and the crude extract is clarified by centrifuging (Christ Cryofuge 6-6 S, 3000 rpm, 1 hour, about 4° C.).

In order to precipitate the interferon, the crude extract is mixed with 430 g/liter of ammonium sulphate and left to stand for 16 hours at 4°-8° C. until precipitation is completed. The precipitate is then recovered by centrifuging (Beckman centrifuge J2-21, Rotor JA10, 10,000 rpm, 60 minutes, 4°-8° C.). The ammonium sulphate pellet is taken up in 145 ml of 0.01 M NaCl and the suspension is adjusted to pH 7.5 with 5 N NaOH. After 3 hours' stirring (cooling with ice) the solution is centrifuged until clear (Beckman J2-21, Rotor JA10, 10,000 rpm, 4° C., 60 minutes) and dialysed against 0.01 M NaCl, using a Nephross-Allegro Dialysis Cartridge (Messrs. Organon) until the interferon solution has an osmolarity of 370 mOsmol/l. Tandem chromatography: For chromatographic purification a column of 75 g of DE-52 cellulose (Whatman) is equilibrated with 0.025 M Tris/HCl+0.2 M NaCl, pH 7.5, and inserted in front of an affinity column (60 ml) which contains the monoclonal antibody EBI-1 (see EP-A-0.119.476), coupled to Sepharose 4B (prepared using BrCN-activated Sepharose 4B, Pharmacia). The affinity column contains 480 mg of the monoclonal antibody EBI-1 and is also equilibrated with Tris/HCl+NaCl, pH 7.5, as described above. The interferon solution is pumped through both columns and washed with 0.025 M Tris/HCl+0.2 M NaCl until only an extinction $OD_{280nm}$ of less than 0.1 is measured in the eluate. Then the preliminary column (DE-52 cellulose) is uncoupled and the EBI-1 column is washed until the eluate is free from protein ($OD_{280nm}$ in the eluate less than 0.01). The adsorbed interferon is then eluted using 0.1 M citric acid in 25% ethylene glycol. The protein peak is collected. The acid eluate from the antibody column is adjusted to pH 4.5 using 2 N ammonia and the precipitate formed is removed by centrifuging.

Figure 6:
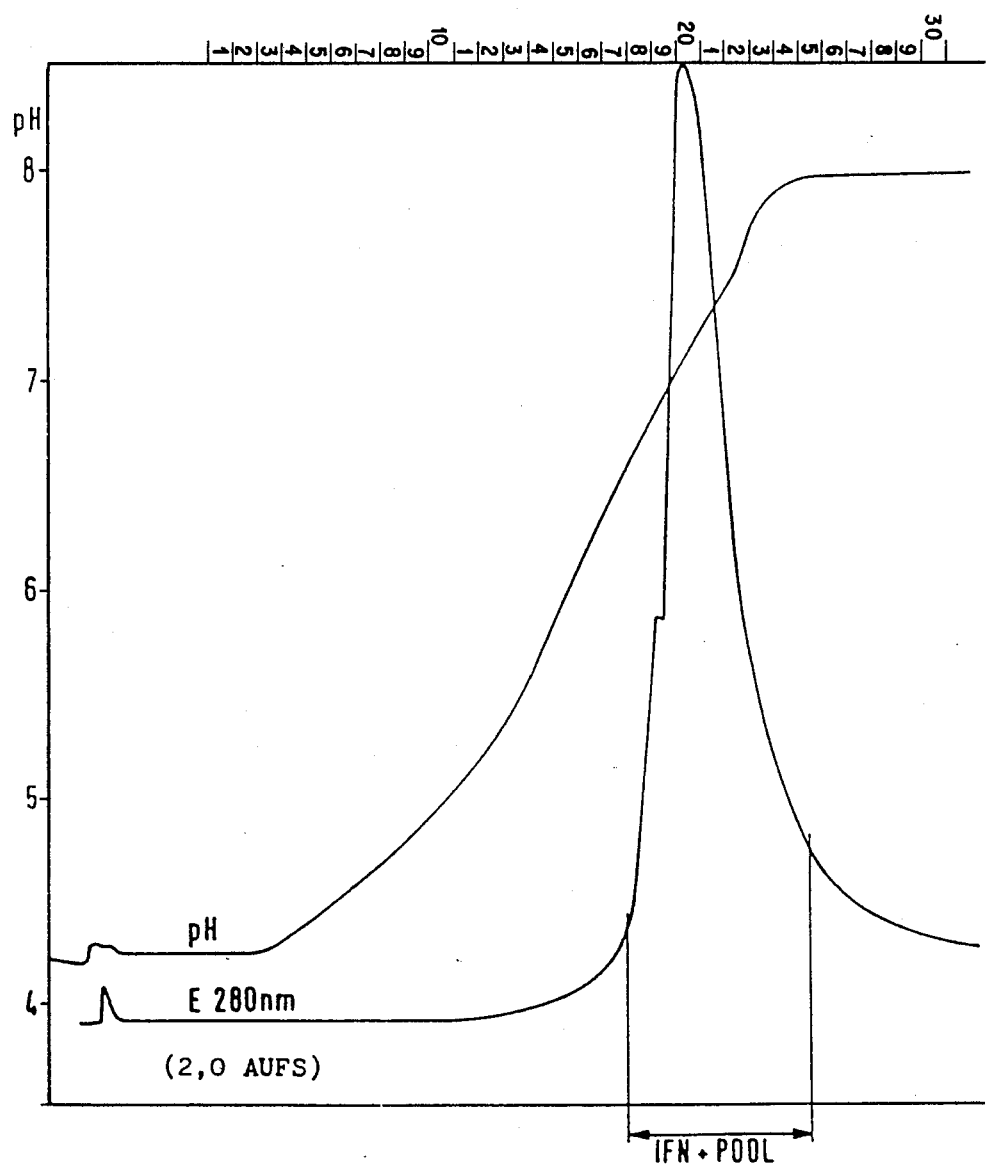
FIG. 6: MONO-S chromatograph of IFN-omegal-/α2(BglII) AUFS=absorption units full scale

The final purification step is ion exchange chromatography on the carrier MONO-S (Pharmacia). A column with a bed volume of 1 ml (HR 5/5) is connected to a FPLC apparatus (Pharmacia) and equilibrated with 0.1 M Na-citrate, pH 4.2. The IFN solution is applied and the interferon adsorbed is eluted by means of a pH gradient (buffer A: 0.1 M Na citrate pH 4.2, and buffer B: 0.1 M Na-phosphate, pH 8.0). The interferon-omegal is eluted at a pH of 7.0 and the IFN peak is collected (see FIG. 6).

Survey of the purification of IFN-omegal/α2(BglII)
Starting material: 145 g of E. coli HB101/pRH78r

| | Vol. (ml) | IFN$^{(x)}$ (units) | Protein$^{(xx)}$ (mg) | Units/ mg | Yield (%) |
|---|---|---|---|---|---|
| Crude extract after ammonium sulphate precipitation and dialysis | 1470 | $16.9 \times 10^9$ | 3000 | $5.6 \times 10^6$ | 100 |
| | 246 | $14.0 \times 10^9$ | 1970 | $7.1 \times 10^6$ | 83 |
| Eluate from the antibody column | 11.1 | $10.3 \times 10^9$ | 12.9 | $800 \times 10^6$ | 61 |
| Supernatant pH 4.5 | 11.9 | $7.4 \times 10^9$ | 9.3 | $800 \times 10^6$ | 44 |

-continued

|  | Vol. (ml) | IFN$^{(x)}$ (units) | Protein$^{(xx)}$ (mg) | Units/ mg | Yield (%) |
|---|---|---|---|---|---|
| Pool after MONO-S | 6.9 | $4.6 \times 10^9$ | 7.0 | $660 \times 10^6$ | 27 |

$^{(x)}$The interferon content is determined by measuring the antiviral activity (CPE reduction test) using A549 cells and encephalomyocarditis virus (EMC virus). Standard used IFN-α2(Arg).
$^{(xx)}$The protein is determined using the Bio-Rad Protein Assay. The standard used is serum albumin.

Assessment of purification

Figure 7:
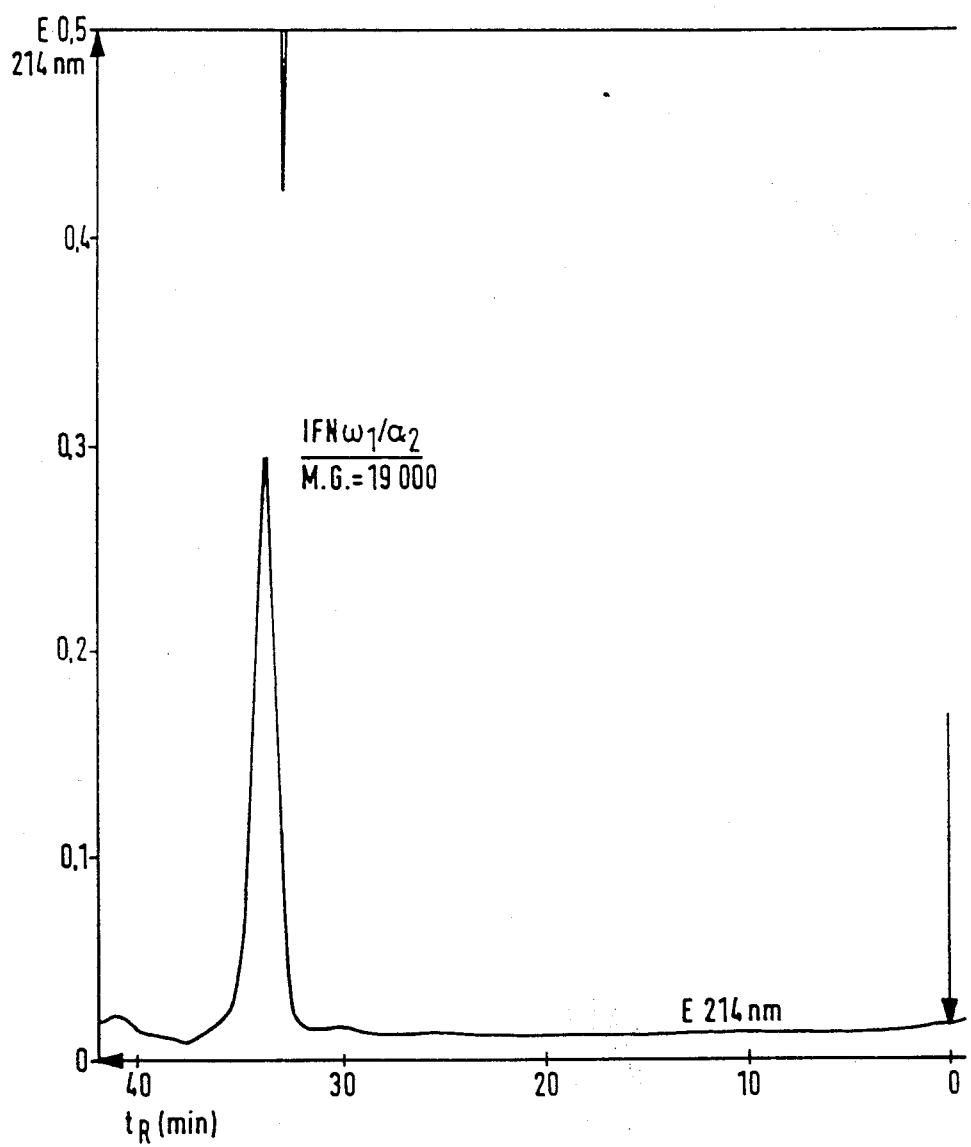
FIG. 7: gel permeation HPLC of IFN-omegal/α2(BglII)

The purified hybrid interferon-omegal/α2(BgII) is homogeneous (cf. FIG. 7 - gel permeation HPLC). The specific activity of abgout $800 \times 10^6$ units/mg of protein attained is higher than that of IFN-α2(Arg) (approx. $300 \times 10^6$ units/mg of protein).

EXAMPLE 10

Preparation of a monoclonal antibody against HuIFN-omegal (a) Immunisation

Two female Balb/c mice about 8 weeks old are immunised with highly purified IFN-omegal/α2(BglII) (purity >95%, dissolved in 0.1 M sodium phosphate/-sodium citrate pH 7) as follows:
  1st immunisation: 100 μg of IFN-omegal/α2(BglII) in an emulsion with complete Freund's adjuvant, by intraperitoneal injection
  2nd immunisation: 100 μg of IFN-omegal/α2(BglII) in an emulsion with incomplete Freund's adjuvant, injected intraperitoneally one month after the 1st immunisation 10 days after the second immunisation blood samples are taken. The ability of the sera to neutralise the antiviral activity of HuIFN-omegal, HuIFN-α2(Arg) and IFN-omegal/α2(BGlII) is tested as follows: 100 μl of a dilution of the serum sample in cell culture medium are mixed with 100 μl of an IFN solution (100 antiviral units/ml) in cell culture medium and incubated for 90 minutes at 37° C. Then the antiviral activity of the samples is determined in a biological test (A549 lung cancer cells, encephalomyocarditis virus):

| Serum dilution | Mouse 1 | | Mouse 2 IFN preparation | | | |
|---|---|---|---|---|---|---|
|  | omega 1 | α2 (Arg) | omegal/ α2 | omega 1 | α2 (Arg) | omegal/ α2 |
| 1:100 | + | + | + | − | − | + |
| 1:1,000 | − | − | + | − | − | +/− |
| 1:10,000 | − | −. | − | − | − | − |

Symbols: + Total neutralisation, +/− partial neutralisation, − no neutralising activity Four weeks after the second immunisation, mouse 1 is given an intravenous injection of a further 100 μg of IFN-omegal/α2(BglII). Three days later the spleen is removed and used to prepare hybridomas. Three weeks after the second immunisation mouse 2 is immunised again; 100 μg of IFN-omegal/α2(BglII) are administered intraperitoneally and 100 μg of onegal/α2(BglII) are administered subcutaneously. Two weeks later another serum sample is taken, which shows a partial neutralising effect on HuIFN-omegal in the test described above at a dilution of 1:100. Four weeks after the third immunisation an intravenous injection of 100 μg of IFN-omegal/α2(BglII) is administered, four days later the spleen is removed and used to prepare hybridomas.

(b) Preparation and screening of hybridomas

Hybridomas are prepared using the method originally developed by Köhler and Milstein (Nature 256, 495 (1975)) using the non-secreting cell line P3×63AG8.653 (Kearney et al., J. Immunol. 123, 1548 (1979)). For fusion, 50% polyethylene glycol 4000 together with 5% dimethylsulphoxide are used. The selection of the hybrid cells in HAT medium is also carried out by known methods (see Monoclonal Antibodies: Production and Maintenance, Lovborg, U., William Heinemann Medical Books, London 1982; Monclonal Antibodies, Hybridomas: A New Dimension in Biological Analyses, ed. Kennet, R. H. McKearn, T. J., and Bechtol, K. B., published by: Plenum Press, N. Y. and London 1980) A total of 730 hybridoma cultures were thus obtained from two fusions. Screening was carried out as follows:

Culture supernatants of at least 10–20% confluent hybridoma cultures were mixed with equal volumes of a solution of HuIFN-omagal (20 antiviral units/ml), incubated for 90 minutes at 37° C. and then tested for their antiviral activity. All cultures were tested at least twice at intervals of one week. Only one of the 730 hybridoma cultures consistently showed a reduction in the antiviral activity in all the tests. This culture, hereinafter referred to as OMG-2, was subcloned by limiting dilution and the subclones were tested again for activity using the test method described. Several positive subclones were inoculated into mice which had been pretreated with Pristane. One of the subclones resulted in the formation of antibody-containing ascites fluid in all the mice. By precipitation with 50% satureated ammonium sulphate solution the antibody obtained was partially purified. The resulting preparation contained antibody at a degree of purity of about 75% (determined by gel permeation high pressure liquid chromatography). About 10 mg of antibody can be obtained from one milliliter of ascites liquid. Further purification up to a degree of purity of more than 95% is achieved by anion exchange chromatography.

(c) Characterisation of the antibody OMG-2

In sodium dodecylsulphate-polyacrylamide gel electrophoresis under non-reducing conditions the antibody OMG-2 has a molecular weight of about 150,000. In gel permeation high pressure liquid chromatography the antibody has a retention capacity identical to that of an IgG marker protein. The antibody is thus probably of the IgG type.

In the neutralisation test (see Example 10b ) the following results were obtained with antibody partially purified by ammonium sulphate procipitation (see Example 10b):

| Antibody concentration μg/ml | IFN preparation | | |
|---|---|---|---|
|  | omega 1 | alpha 2 | omega 1/α2 |
| 5 000 | +/− | +/− |  |
| 1 000 | − | − | + |

| Antibody concentration | IFN preparation | | |
|---|---|---|---|
| μg/ml | omega 1 | alpha 2 | omega 1/α2 |
| 100 | − | − | + |
| 10 | − | − | +/− |
| 1 | | | − |

Thus, the antibody has a powerful neutralising effect on the hybrid IFN-omegal/α2(BglII) used to immunise the mice, but its effect on HuIFN-α2(Arg) and HuIFN-omegal is approximately 500 times weaker. In spite of the obviously relatively slight affinity for HuIFN-omegal, the antibody OMG-2 can be used successfully for the immune affinity chromatography of this interferon (see Example 11).

EXAMPLE 11

Purification of IFN-omegal (a) Extraction and CPG chromatography: 794 g of acid-precipitated *E. coli*, deep frozen at −20° C., of the clone pRHW14 are stirred into 7700 ml of 1% acetic acid, whilst cooling with ice, until the material is fully distributed (about 30 minutes) and adjusted to pH 10 using 2 N NaOH. After stirring for 2 hours whilst cooling with ice, the suspension is adjusted to pH 7.5 (2 N HCL) and centrifuged until clear (1 hour at 10,000 rpm, 4° C., JA 10-rotor in the Beckman centrifuge J2-21). The clear supernatant is pumped at a rate of 50 ml per hour through a 500 ml column of CPG (controlled pore glass, CPG 10-350, 120-200 mesh, Electro-Nucleonics Inc., USA) and then the column is thoroughly washed with 0.025 M Tris/HCl + 1 M NaCl (pH 7.5). The interferon adsorbed on the column is then eluted with 0.025 M Tris/HCl + 1 M KSCN in 50% ethyleneglycol (pH 7.5) (50 ml per hour). The IFN pool is then dialysed agianst 0.025 M Tris/HCl + 0.1 M NaCl, whilst the IFN pool is simultaneously concentrated by the addition of 10% polyethylene glycol 40,000 to the external solution. The dialysed concentrate is clarified by centrifuging (1 hour, 4° C., 15,000 rpm, JA-20 rotor in the Beckman centrifuge J2-20).

(b) Affinity chromatography on OMG 2-sepharose

Purified monoclonal antibody OMG-2 is coupled to the carrier Sepharose 4B by means of BrCN-activated Sepharose 4B in accordance with the manufacturer's instructions (Pharmacia). 16 mg of the monoclonal antibody are used for each gram of activated Sepharose 4B. An affinity column with a volume of 8 ml is used for the separation described.

The concentrate from the CPG column according to Example 11a is pumped through the affinity column at 4 ml per minute and the column is then washed with 0.025 M Tris/HCl + 0.1 M NaCl, pH 7.5, until the eluate is free from protein (OD$_{280}$nm of the eluate identical to that of the washing buffer). The bound interferon is then eluted at the rate of 2 ml/minute using 0.1 M citric acid in 25% ethylene glycol and the protein peak (OD$_{280}$nm) is collected.

(c) Ion exchange chromatography on the carrier NONO-S

Figure 8:
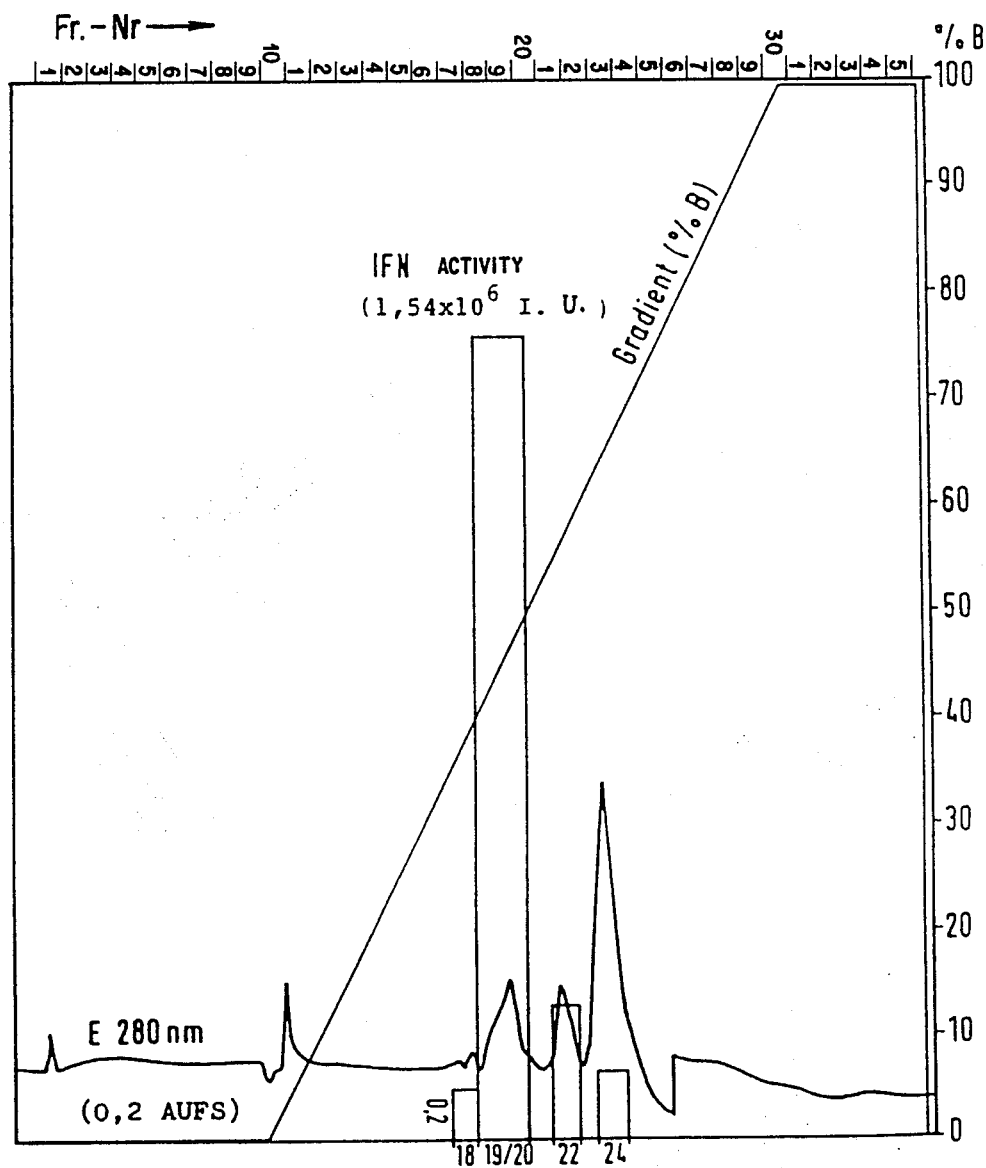
FIG. 8: MONO-S chromatograph of IFN-omegal

A 1 ml column (HR 5/5) of the carrier material MONO-S (both made by Pharmacia) coupled to an FPLC apparatus (Pharmacia) is used. The ion exchange column is equilibrated with 0.1 M K-phosphate, pH 6.0, in 25% propylene glycol and the eluate from the affinity column obtained according to Example 11b is pumped through at the rate of 0.5 ml/minute. The adsorbed interferon is then eluted using an NaCl gradient (buffer B: 0.1 M K-phosphate + 1 M NaCl, pH 6.0, in 25% propylene glycol). The fractions (1 ml each) are tested for interferon activity. The first peak (OD$_{280}$nm) at 46% of buffer B contains interferon-omega (see FIG. 8).

(d) Reverse phase HPLC

A Bakerbond WP-RP 18 column, 4×250 mm, with a particle diameter of 5 microns and a pore diameter of 300 Å is used as the stationary phase. The mobile phase is a gradient of acetonitrile in 0.1% trifluoroacetic acid:
Buffer A: 0.1% trifluoroacetic acid in water,
Buffer B: 0.1% trifluoroacetic acid in acetonitrile,
Gradient of 20–68% B in 28 minutes,
Flow rate: 1 ml/minute
Detection: OD$_{214}$nm.

Figure 9:
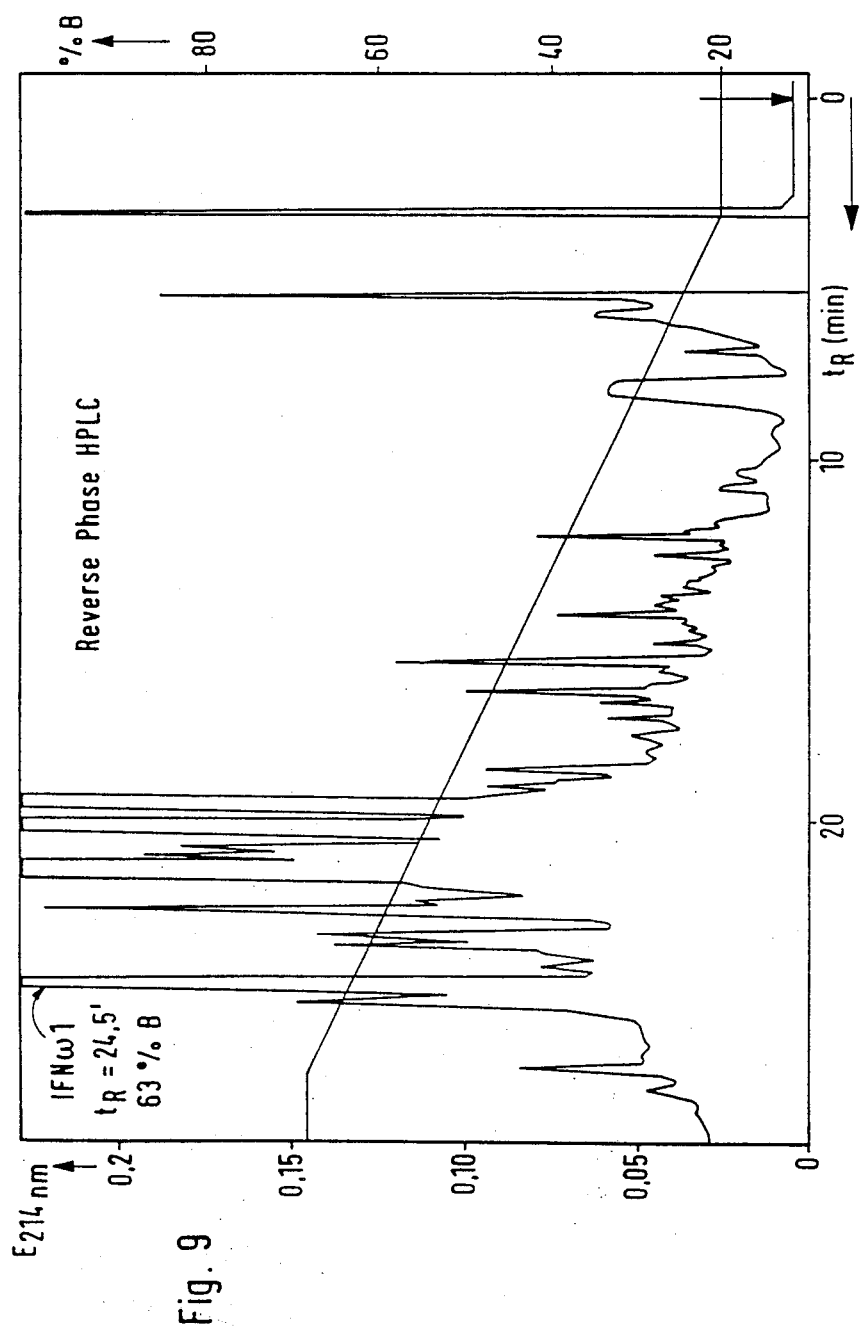
FIG. 9: reverse phase HPLC of IFN-omegal Thus, the new BglII hybrid interferons and the N-glycosylated derivatives thereof consist either of amino acids 1–66 of an α1 or α2 interferon, preferably of amino acids 1–65 of IFN-α2(Arg), and the amino acids 67 to 173 of an omegal interferon, or of the amino acids 1 to 66 of omegal interferon and amino acids 67 to 167 of an α1 or α2-interferon, preferably of amino acids 66 to 166 of IFN-α2(Arg), whilst the N-terminal Met group is usually split off again after the bacterial protein synthesis.

630 μg of the protein obtained according to Example 11c (IFN pool according to MONO-S) are applied. The eluate is tested in the range from 48–65% B, The interferon omegal is eluted with a retention time of 24.5 minutes and 63% of buffer B (see FIG. 9). The yield is 5 to 10 μg and the specific activity is $>10^8$ units/mg of protein.

(e) Determining the N-terminal amino acid sequence

The IFN-omegal peak (RP-HPLC) obtained according to Example 11d is dried in a Speedvac centrifuge and analysed in a type 470 A sequencer (Applied Biosystems). The following amino acid sequence is obtained:

Xxx—Asp—Leu—Pro—Gln—Asn—Xxx—Gly—Leu—Leu—Ser—
1                       5                    10

This sequence confirms the order of the amino acids derived from the cDNA (cysteine at the 1st position cannot be detected without reduction and alkylation of the protein and histidine at the 7th position could not be clearly detected).

Summary of the purification of IFN-omegal

| | Vol. (ml) | IFN$^{(x)}$ (units) | Protein$^{(xx)}$ (mg) | Units/ mg | Yield (%) |
|---|---|---|---|---|---|
| 1. Extraction and CPG chromatography | | | | | |
| Crude extract | 7700 | 190 × 10$^6$ | 19.100 | 9.950 | 100 |
| Pool after CPG | 425 | 53 × 10$^6$ | 4.600 | 11.500 | 28 |
| after dialysis | 410 | 45 × 10$^6$ | 1.650 | 27.300 | 24 |
| 2. Affinity chromatography on OMG 2-Sepharose | | | | | |
| applied | 350 | 40.6 × 10$^6$ | 1.520 | 26.700 | 100 |
| not absorbed | 440 | 4.5 × 10$^6$ | — | — | 11 |
| Eluate IFN-omega | 7 | 25.6 × 10$^6$ | 2.84 | 9.0 × 10$^6$ | 63 |
| 3. Ion exchange chromatography on MONO-S | | | | | |
| applied | 7 | 7.14 × 10$^6$ | 2.84 | 2.5 × 10$^6$ | 100 |
| IFN omega pool | 2 | 3.04 × 10$^6$ | 0.72 | 4.2 × 10$^6$ | 43 |

$^{(x)}$The interferon content is determined by measuring the antiviral activity (CPE reduction test) using A 549 cells and encephalo-myocarditis virus (EMC virus). Standard: rIFN-α2(Arg). This is the average from three independent tests.
$^{(xx)}$The protein is determined by the Bio-Rad Protein Assay. The standard is serum albumin.

We claim:
1. A hybriod interferon the formula

$R^1$—Gln Ile Phe—$R_2$      (I)

wherein $R_1$ is a polypeptide fragment encoded by a DNA sequence upstream of the BglII restriction site common to alpha 1-, alpha 2-, and omega-interferons, wherein said polypeptide fragment is selected from the group consisting of the corresponding fragments of
- an alpha-1 interferon,
- the N-terminal Met derivative of an alpha-1 interferon,
- the N-formyl-Met derivative of an alpha-1-interferon,
- an alpha-2 interferon,
- the N-terminal Met derivative of an alpha-2 interferon,
- the N-formyl-Met derivative of an alpha-2 interferon,
- an omega interferon,
- the N-terminal Met derivative of an omega interferon, or
- the N-terminal formyl-Met derivative of an omega interferon, and $R_2$ is a polypeptide fragment encoded by a DNA sequence downstream of said BglII restriction site wherein said polypeptide fragment is selected from the group consisting of the corresponding fragments of

- an alpha-1 interferon,
- an alpha-2 interferon, or
- an omega interferon, with the proviso only one of $R_1$ and $R_2$ is derived from an omega interferon.

2. The hybrid interferon of claim 1 wherein
$R_1$ is a polypeptide fragment of an alpha-2-interferon and $R_2$ is a polypeptide fragment of an omegal-interferon; or
$R_1$ is a polypeptide fragment of an omegal-interferon and $R_2$ is a polypeptide fragment of an alpha-2-interferon.

3. The hybrid interferon of claim 1, wherein said hybrid interferon is glycosylated.

4. The hybrid interferon of claim 1, wherein said omega interferon is selected from the group consisting of omegal (Glu) or omegal (Gly) interferon.

5. A hybrid interferon of the formula:

|     |     |     |     | 5   |     |     |     |     | 10  |     |     |     |     | 15  |
| --- | --- | --- | --- | --- | --- | --- | --- | --- | --- | --- | --- | --- | --- | --- |
| Cys | Asp | Leu | Pro | Gln | Thr | His | Ser | Leu | Gly | Ser | Arg | Arg | Thr | Leu |
|     |     |     |     | 20  |     |     |     |     | 25  |     |     |     |     | 30  |
| Met | Leu | Leu | Ala | Gln | Met | Arg | Arg | Ile | Ser | Leu | Phe | Ser | Cys | Leu |
|     |     |     |     | 35  |     |     |     |     | 40  |     |     |     |     | 45  |
| Lys | Asp | Arg | Arg | Asp | Phe | Gly | Phe | Pro | Gln | Glu | Glu | Phe | Gly | Asn |
|     |     |     |     | 50  |     |     |     |     | 55  |     |     |     |     | 60  |
| Gln | Phe | Gln | Lys | Ala | Glu | Thr | Ile | Pro | Val | Leu | His | Glu | Met | Ile |
|     |     |     |     | 65  |     |     |     |     | 70  |     |     |     |     | 75  |
| Gln | Gln | Ile | Phe | Ser | Leu | Phe | His | Thr | Glu | Arg | Ser | Ser | Ala | Ala |
|     |     |     |     | 80  |     |     |     |     | 85  |     |     |     |     | 90  |
| Trp | Asn | Met | Thr | Leu | Leu | Asp | Gln | Leu | His | Thr | Gly | Leu | His | Gln |
|     |     |     |     | 95  |     |     |     |     | 100 |     |     |     |     | 105 |
| Gln | Leu | Gln | His | Leu | Glu | Thr | Cys | Leu | Leu | Gln | Val | Val | Gly | Glu |
|     |     |     |     | 110 |     |     |     |     | 115 |     |     |     |     | 120 |
| Gly | Glu | Ser | Ala | —X— | Ala | Ile | Ser | Ser | Pro | Ala | Leu | Thr | Leu | Arg |
|     |     |     |     | 125 |     |     |     |     | 130 |     |     |     |     | 135 |
| Arg | Tyr | Phe | Gln | Gly | Ile | Arg | Val | Tyr | Leu | Lys | Glu | Lys | Lys | Tyr |
|     |     |     |     | 140 |     |     |     |     | 145 |     |     |     |     | 150 |
| Ser | Asp | Cys | Ala | Trp | Glu | Val | Val | Arg | Met | Glu | Ile | Met | Lys | Ser |
|     |     |     |     | 155 |     |     |     |     | 160 |     |     |     |     | 165 |
| Leu | Phe | Leu | Ser | Thr | Asn | Met | Gln | Glu | Arg | Leu | Arg | Ser | Lys | Asp |
|     |     |     |     | 170 |     |     |     |     |     |     |     |     |     |     |
| Arg | Asp | Leu | Gly | Ser | Ser |     |     |     |     |     |     |     |     |     | wherein x is selected from the group consisting of Gly or Glu.

6. A hybrid interferon of the formula:

|     |     |     |     | 5   |     |     |     |     | 10  |     |     |     |     | 15  |
| --- | --- | --- | --- | --- | --- | --- | --- | --- | --- | --- | --- | --- | --- | --- |
| Cys | Asp | Leu | Pro | Gln | Asn | His | Gly | Leu | Leu | Ser | Arg | Asn | Thr | Leu |
|     |     |     |     | 20  |     |     |     |     | 25  |     |     |     |     | 30  |
| Val | Leu | Leu | His | Gln | Met | Arg | Arg | Ile | Ser | Pro | Phe | Leu | Cys | Leu |
|     |     |     |     | 35  |     |     |     |     | 40  |     |     |     |     | 45  |
| Lys | Asp | Arg | Arg | Asp | Phe | Arg | Phe | Pro | Gln | Glu | Met | Val | Lys | Gly |
|     |     |     |     | 50  |     |     |     |     | 55  |     |     |     |     | 60  |
| Ser | Gln | Leu | Gln | Lys | Ala | His | Val | Met | Ser | Val | Leu | His | Glu | Met |
|     |     |     |     | 65  |     |     |     |     | 70  |     |     |     |     | 75  |
| Leu | Gln | Gln | Ile | Phe | Asn | Leu | Phe | Ser | Thr | Lys | Asp | Ser | Ser | Ala |
|     |     |     |     | 80  |     |     |     |     | 85  |     |     |     |     | 90  |

| | | | | | | | | | | | | | | |
|---|---|---|---|---|---|---|---|---|---|---|---|---|---|---|
| Ala | Trp | Asp | Glu | Thr | Leu | Leu | Asp | Lys | Phe | Tyr | Thr | Glu | Leu | Tyr |
| | | | | 95 | | | | | 100 | | | | | 105 |
| Gln | Gln | Leu | Asn | Asp | Leu | Glu | Ala | Cys | Val | Ile | Gln | Gly | Val | Gly |
| | | | | 110 | | | | | 115 | | | | | 120 |
| Val | Thr | Glu | Thr | Pro | Leu | Met | Lys | Glu | Asp | Ser | Ile | Leu | Ala | Val |
| | | | | 125 | | | | | 130 | | | | | 135 |
| Arg | Lys | Tyr | Phe | Gln | Arg | Ile | Thr | Leu | Tyr | Leu | Lys | Glu | Lys | Lys |
| | | | | 140 | | | | | 145 | | | | | 150 |
| Tyr | Ser | Pro | Cys | Ala | Trp | Glu | Val | Val | Arg | Ala | Glu | Ile | Met | Arg |
| | | | | 155 | | | | | 160 | | | | | 165 |
| Ser | Phe | Ser | Leu | Ser | Thr | Asn | Leu | Gln | Glu | Ser | Leu | Arg | Ser | Lys |
| | | | | 170 | | | | | | | | | | |
| Glu. | | | | | | | | | | | | | | |

7. A pharmaceutical composition, comprising an artiviral effective amount of the hybrid interferon of claim 1 and a pharmaceutically acceptable carrier.

8. A method of treating a viral disease in a patient, comprising administering the pharmaceutical composition of claim 7 to a patient.

* * * * *